United States Patent
Davidson et al.

(10) Patent No.: US 9,872,890 B2
(45) Date of Patent: Jan. 23, 2018

(54) DETERMINING INSULIN DOSING SCHEDULES AND CARBOHYDRATE-TO-INSULIN RATIOS IN DIABETIC PATIENTS

(76) Inventors: Paul C. Davidson, Atlanta, GA (US); Harry R. Hebblewhite, Atlanta, GA (US)

( * ) Notice: Subject to any disclaimer, the term of this patent is extended or adjusted under 35 U.S.C. 154(b) by 0 days.

(21) Appl. No.: 10/804,825

(22) Filed: Mar. 19, 2004

(65) Prior Publication Data

US 2005/0049179 A1    Mar. 3, 2005

Related U.S. Application Data

(60) Provisional application No. 60/456,271, filed on Mar. 19, 2003, provisional application No. 60/532,487, filed on Dec. 26, 2003, provisional application No. 60/543,576, filed on Feb. 11, 2004.

(51) Int. Cl.

| | |
|---|---|
| *G01N 33/48* | (2006.01) |
| *A61K 38/28* | (2006.01) |
| *G06F 19/00* | (2011.01) |
| *G06Q 50/24* | (2012.01) |
| *A61B 5/145* | (2006.01) |

(52) U.S. Cl.
CPC .......... *A61K 38/28* (2013.01); *G06F 19/3468* (2013.01); *G06F 19/3481* (2013.01); *G06Q 50/24* (2013.01); *A61B 5/14532* (2013.01)

(58) Field of Classification Search
None
See application file for complete search history.

(56) References Cited

U.S. PATENT DOCUMENTS

| | | | | |
|---|---|---|---|---|
| 5,822,715 | A * | 10/1998 | Worthington et al. | 702/19 |
| 6,024,699 | A | 2/2000 | Surwit | |
| 6,551,276 | B1 * | 4/2003 | Mann | A61M 5/14244 604/131 |
| 2003/0028089 | A1 * | 2/2003 | Galley et al. | 600/365 |
| 2003/0055570 | A1 * | 3/2003 | Ribeiro, Jr. | 702/19 |

OTHER PUBLICATIONS

Doyle et al., Proceedings of the 23rd Annual EMBS International Conference, Istambul, Turkey, Oct. 2001, p. 1-4.*
Albisser et al., Medical & Biological Engineering & Computing, 1986, vol. 24, p. 577-584.*
Kaufman et al., Diabetes Metab. Res. Rev., 1999, vol. 15, p. 338-352.*
Medtronic Paradigm Infusion Pump User Guide (Copyright 2005; pp. 1-170).*
Piwernetz, R., et al., Glucose Control in Mobile type 1 (Insulin-Dependent) Diabetic Patients by Mans of a Semi-Automatic Feedback Controlled Insulin Infusion System, Diabetologia, 1982, vol. 23, p. 229-234.
Supplemental European Search Report in Application No. 04757881.0-1225 dated Oct. 18, 2011.
Bode, et al. "Continuous glucose monitoring used to adjust diabetes therapy improves glycosylated hemoglobin: a pilot study," Diabetes Research and Clinical Practice 46 (1999), pp. 183-190.
Lehmann, et al. "AIDA2: A Mk. II automated insulin dosage advisor," J. Biomed. Eng., vol. 15, May 1993, pp. 201-211.
Deutsch, et al. "Computer-assisted diabetic management: a complex approach," Computer Methods and Programs in Biomedicine, 32, 1990, pp. 195-214

* cited by examiner

Primary Examiner — Pablo S Whaley
(74) Attorney, Agent, or Firm — Thomas I Horstemeyer, LLP

(57) ABSTRACT

Method for digitally determining the daily insulin regimen for a diabetic patient. The invention divides the patient's day into adjustable time intervals containing basal insulin dosage rates and Carbohydrate-to-Insulin Ratio(s) (for determining meal insulin doses). The invention identifies the Corrective Insulin doses over a time interval as an "error" in the Prescription Insulin (Basal Insulin+Meal Insulin). Methods involve first estimating the change to one of these two components of Prescription Insulin, and then determining the change to the other by subtracting from the error. One method estimates Change in Meal Insulin distributed among intervals proportional to old Meal Insulin. Another method lumps After-Meal Corrective Insulin together with Meal Insulin. Another method splits the interval at the After-Meal Corrective Dose and determines Basal from Time-Boundary Corrective Dose. Data may be obtained from the previous day, and a small fraction of error applied, leading to asymptotic reduction of error. Data may be obtained from recent history, and a larger fraction of error applied by doctor or automatic method.

16 Claims, 3 Drawing Sheets

Figure 1: The first screen of Version 6.2.1.1.3, Digital Advisor for Practitioner, using Multiple Days' Data from pump type D. Outer panel is demographic data from table Tp. Inner panel is for patient's interaction with practitioner on a certain date. Inner Panel has two screens. This is the first, showing un-scheduled data.

Figure 2: The second screen of Version 6.2.1.1.3, Digital Advisor for Practitioner, using Multiple Days' Data from Pump Type D. This is second screen, which showing data that follows a daily schedule.

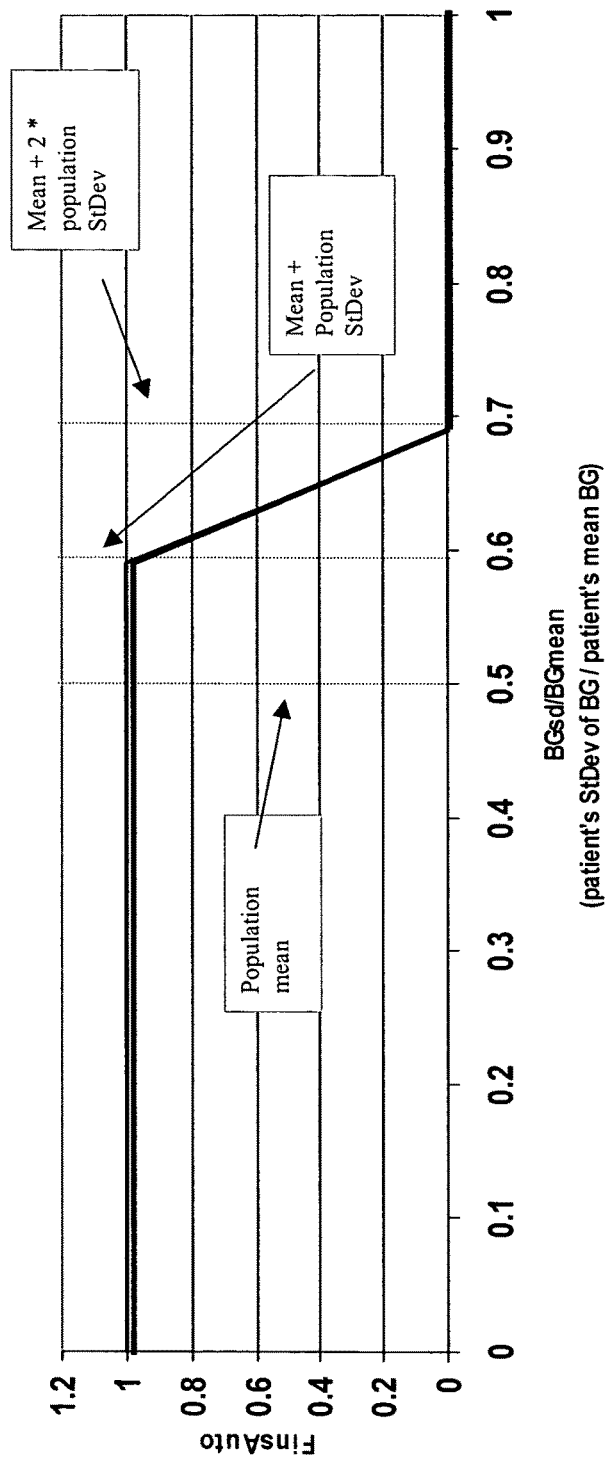
Figure 3: The multiplier FInsAuto, which automates deRxInsAuto in Automated Multiple Days' Data Version by comparing the standard deviation of the patient's BGs to the mean standard deviation from the database. The result is used as follows:
$$deRxInsAuto = FInsAuto * KrxInslMax * TBCorTot$$

DETERMINING INSULIN DOSING SCHEDULES AND CARBOHYDRATE-TO-INSULIN RATIOS IN DIABETIC PATIENTS

RELATED APPLICATION

This application claims priority to and the benefit of provisional applications, Ser. No. 60/456,271 filed Mar. 19, 2003, Ser. No. 60/532,487 filed Dec. 26, 2003, and Ser. No. 60/543,576 filed Feb. 11, 2004.

FIELD OF THE INVENTION

The invention relates generally to the field of digital aids to assist in the treatment of diabetic patients who use insulin pumps or multiple dosing insulin regimens and provides a method for determining insulin dosing schedules in diabetic patients.

BACKGROUND OF THE INVENTION

Diabetes Mellitus has been treated for many years by insulin injection. Three recent advances are changing diabetes care: The Insulin Pump, new insulin formulas for Multiple Dose Injection, and Inhaled Insulin. These are discussed below:

THE INSULIN PUMP: The invention of the insulin pump revolutionized diabetes care. It is a battery-powered device about the size of a pager. It contains a cartridge of insulin and pumps the insulin through a flexible tube into the patient via an "infusion set", which is a small plastic needle or "canula" fitted with an adhesive patch. The invention of the pump makes it possible to adopt a typical insulin regimen as follows: Basal Insulin is injected slowly and continuously at a rate that can be programmed to change multiple times during the day (about 4 or 5 changes per day is common). Between the changes, the Basal Insulin Rate of infusion is constant. The constant periods are called "intervals". Additionally, boluses of insulin can be injected on command by the patient. There are two main types of boluses:

Meal Boluses are infused just before a meal in an amount, proportional to the glycemic effect of the meal. This is generally proportional to the number of grams of carbohydrate in the meal. The proportionality constant is a personalized number called the Carbohydrate-to-Insulin Ratio, CIR. It is used as follows:

$$\text{Meal Insulin Bolus} = (\text{grams of carbohydrates in the meal})/\text{CIR} \quad (1)$$

This calculation is generally performed by the patient, but there are pump models that can store the patient's CIR in memory and require only the grams of carbohydrate in the meal as the input.

Correction Boluses are infused immediately after a Blood Glucose test has been performed; the amount of the correction bolus is proportional to the error in the blood glucose concentration from the patient's personalized Target Blood Glucose. The proportionality constant is a personalized number called the Correction Factor, CF. It is used as follows:

$$\text{Corrective Insulin Bolus} = (\text{Blood Glucose concentration} - \text{Target})/\text{CF} \quad (2)$$

There are two types of Corrective Bolus, each with a different Target:

Time-Boundary Corrective Insulin Boluses are administered in a fasting state at the end of a time interval.

After-Meal Corrective Boluses are administered from one to five hours after a meal, most often within the time interval.

Recently, pump manufacturers have been incorporating digital features in their pumps that make treatment easier. Some pumps can store the values of CF and Target and require only the Blood Glucose Concentration (BG) as input. Among these new digital features is the "Insulin-On-Board" feature. This feature mathematically models the amount of insulin still in the body at a given time after a bolus and recommends reductions to the boluses accordingly. This feature makes After-Meal Corrective Boluses more safe and practical.

MULTIPLE DOSE INJECTION (MDI): Advances are being made in developing different types of insulin. Some are very long acting and non-peaking. The long-acting insulin can be injected as infrequently as once per day in a regimen very similar to a pump patient's basal insulin regimen. Injections of rapid-acting types of insulin can be given as meal and correction boluses. The two types together act as a system. These insulins are available in portable "pens" (named for their resemblance to writing implements). The pens have been mated with BG meters in "kits" in which the devices communicate so that the combined memory is stored in one of the two devices in the "kit".

INHALED INSULIN: Inhaled insulin delivery systems are under development for short-acting insulin. It is expected that the inhalers will be combined with BG meters into "kits" like the ones used for MDI, then the present invention will be able to handle inhaled insulin in the same manner. This development is expected in the future.

The nature of diabetes care is very quantitative. Ironically, the proliferation of numbers makes the use of lengthy algorithms on pocket calculators too time-consuming and therefore prohibitively expensive. The majority of endocrinologists, therefore, use experience-based subjective methods. In the interest of providing greater subjective feel for the case at hand, endocrinologists often use the numbers to simply help them discern trends; then treat the trends. For instance, they commonly view the blood glucose (BG) scatter charts and printouts to discern trends by such subjective means as the visual density of dots on the BG scatter chart and the relative location of the areas of highest density. They translate these trends into insulin dose changes using their experience.

Experienced-based and subjective methods are often not uniform from one practitioner to the next. Additionally, there is a shortage of endocrinologists and other diabetes specialists. Accordingly, the management of diabetes is done in a disorganized manner by clinicians of widely varying degrees of expertise. The result is that control of diabetes in most patients, while satisfactory, is not optimal. As a result of sub-optimal BG control, the course of diabetes can include complications involving all body systems. These complications are associated with premature mortality and are associated with a cost, which amounts to 19% of the health dollars to care for 6% of the population.

BRIEF SUMMARY OF THE INVENTION

The present invention overcomes the aforementioned disadvantages of current care, by providing a method to analyze and prescribe changes to the daily insulin-dosing schedule of diabetic patients using insulin pumps, multiple-dose subcutaneous injection, or inhaled insulin. The method divides the patient's day into selected time intervals in which adjustable schedules are provided for Basal Insulin dosage rates and Carbohydrate-to-Insulin Ratio(s) (to determine Meal Insulin doses). The time boundaries and Basal Rate changes are usually set by the Practitioner to coincide with the patient's meals. The patients are usually encouraged to test their Blood Glucose (BG) at the time boundaries just before they eat. The invention uses two systems of insulin nomenclature:

Conventional Insulin Nomenclature:

Total Daily Insulin=Prescription Insulin+Corrective Insulin   (3)

where: Prescription Insulin=Basal Insulin+Meal Insulin   (4)

The invention incorporates the concept of utilizing the Corrective Insulin over a selected time interval as an "error" in the patient's Prescription Insulin (Basal Insulin+Meal Insulin) for the whole day as well as for each time interval. Methods are included for estimating the change to one of the two components of Prescription Insulin, then determining the change to the other component by subtracting from the error. Therefore, there are two basic algorithmic forms, which are called "Floats":

The MealIns Float:

The change in Basal Insulin is estimated first; then the invention calculates the change in Meal Insulin to be the error in Prescription Insulin minus the change in Basal Insulin. Some of the ways for estimating the change in Basal Insulin are:

Borrowing Basal Rate from another interval;
Estimating Basal Rate from another algorithm (e.g. a Basal Float);
Estimating change in Basal Insulin from the carb-free latter part of a time interval using the Time-Boundary Corrective Insulin (at the end of the interval) as the error indicator. The float is done on the first part of the interval, using the After-Meal Corective Insulin as the error or The Basal Float:

The change in Meal Insulin is estimated first; then the invention calculates the change in Basal Insulin to be the error in Prescription Insulin minus the change in Meal Insulin. Some of the ways for estimating the change in Meal Insulin are:

Borrowing Meal Insulin or CIR from another interval;
Estimating the change in Meal Insulin for an interval as a share of the Change in Total Day's Meal Insulin in the same proportion as (Carbs for the interval)/(Total Day's Carbs);
Estimating the change in Meal Insulin for an interval as a share of the Change in Total Day's Meal Insulin in the same proportion as (Meal Insulin for the interval)/(Total Day's Meal Insulin).

Enhanced Insulin Nomenclature:

Also, to provide another way of accounting for After-Meal Insulin, the invention identifies "Enhanced Variables" as a system of insulin nomenclature that lumps the After-Meal Corrective Insulin with the Meal Insulin as follows:

Total Daily Insulin=Enhanced Prescription Insulin+ Time-Boundary Corrective Insulin   (5)

where

Enhanced Prescription Insulin=Basal Insulin+Enhanced Meal Insulin   (6)

and:

Enhanced Meal Insulin=Meal Insulin+After-Meal Corrective Insulin   (7)

The Floats are very similar:

The MealIns Float:

The change in Basal Insulin is estimated first; then the invention calculates the change in Enhanced Meal Insulin to be the error in Enhanced Prescription Insulin minus the change in Basal Insulin. Some of the ways for estimating Basal Insulin are:

Borrowing Basal Rate from another interval
Estimating Basal Rate from another algorithm (e.g. a Basal Float)

or

The Basal Float:

The change in Enhanced Meal Insulin is estimated first; then the invention calculates the change in Basal Insulin to be the error in Enhanced Prescription Insulin minus the change in Enhanced Meal Insulin. Some of the ways for estimating Enhanced Meal Insulin are:

Borrowing Enhanced Meal Insulin or CIR from another interval;
Estimating the change in Enhanced Meal Insulin for an interval as a share of the Change in Total Day's Enhanced Meal Insulin in the same proportion as (Carbs for the interval)/(Total Day's Carbs);
Estimating the change in Enhanced Meal Insulin for an interval as a share of the Change Total Day's Enhanced Meal Insulin in the same proportion as (Enhanced Meal Insulin for the interval)/(Total Day's Enhanced Meal Insulin);

In General:

It may not be desirable to apply all of the error term to effect a change. Methods are included for applying a limited amount of the error in order to avoid overshoots.

The above selection of "Float" algorithms have been developed in two main versions:

Daily Update Version: The Float algorithms above are embodied in a program that uses the previous day's data to make calculations for the present day. In this version, the full amounts of the error terms are not applied, but instead a predetermined fraction of the error terms are applied. If the error was valid, a reduced amount of it will show-up the next day. This next day's reduced error will be reduced by the same fraction and so on until the error disappears asymptotically. This version is especially well-suited for installation in insulin pumps, inhaled insulin kits, MDI injection kits, PDA's and other portable devices.

Multiple Days' Data Version: The Float algorithms above are embodied in a program that uses the recent calendar period (e.g. last few weeks) for the data source. The data are therefore averages. The full amounts of the error terms are not necessarily applied, but instead the fraction or amount of error to be applied is input by the practitioner. These versions are suitable for installation in the practitioner's computer. A sub-version of this version determines the error fractions automatically. It is suitable for the patients' computer, or a website, for use with patients who have insulin pumps, or kits for Multiple Daily Injection or Inhaled Insulin.

The various aspects of the present disclosure may be more clearly understood and appreciated from a review of the following detailed description of the disclosed embodiments and by reference to the appended figures.

BRIEF DESCRIPTION OF THE FIGURES

FIG. 1 illustrates an exemplary embodiment of the Input Form for the Multiple Days' Data Version for Insulin Pumps (Type D). The inner panel is the SubForm. It has two pages, which can be reached by scrolling. The first of these is shown. It contains single-valued data (not scheduled data).

FIG. 2 illustrates an exemplary embodiment of the Input Form for the Multiple Days' Data Version for Insulin Pumps (Type D). The inner panel is the SubForm. It has two pages, which can be reached by scrolling. The second of these is shown. It contains daily schedule data.

FIG. 3 an exemplary embodiment of the source of the multiplier FinsAuto, which automates dRxInsAuto in the automated Multiple Days' Data Version (Automatic Digital Advisor) by comparing the standard deviation of the patient's BGs to the mean standard deviation from the database. If the patient's number is high, the multiplier (which is always <1) is reduced. The automated change in Enhanced Prescription Insulin is FinsAuto times the Time-Boundary Corrective Insulin times another factor.

DETAILED DESCRIPTION OF THE INVENTION

1. Table of Contents

The invention is a set of algorithms used to determine the various insulin-dosing rates, and Carbohydrate-to-Insulin Ratio(s) that comprise the daily insulin-dosing schedule for a patient. The "Float Algorithms" apply to all exemplary embodiments described herein. The description, as shown in the table of contents below, is broken down first by "Embodiment" (pump or MDI) and then by "Version" (Daily Update or Multiple Day's Data) and finally by "Algorithm" (Basal Float1, Meal Insulin Float 1, etc).

1. TABLE OF CONTENTS
2. SUFFIXES and TIME INDICES
3. GLOSSARY
4. GENERIC DERIVATIONS
   4.1 MAKING CHANGES IN THE CARBOHDRATE-TO-INSULIN RATIO, CIR
   4.2 SOME IMPORTANT EQUATIONS
   4.2.1 CONVENTIONAL INSULIN NOMENCLATURE
   4.2.2 ENHANCED INSULIN NOMENCLATURE:
   4.2.3 GENERAL
   4.3 THE TWO-LEVEL BASAL SYSTEM, and the Kf CALCULATOR
   4.3.1 STATISTICAL CORRELATION
   4.3.2 AVERAGING
5. TYPES OF INSULIN DELIVERY SYSTEMS
6. DESCRIPTION BY, VERSION, EMBODIMENT, ALGORITHM
   6.1 VERSIONS USING DAILY UPDATE
   6.1.1 PRELIMINARY DERIVATIONS
      6.1.1.1 TIME INTERVALS AND CORRECTIVE INSULIN
      6.1.1.2 KrxInsl: GOVERNS THE SIZE OF INSULIN CHANGES
   6.1.2 FOR PUMPS (TYPE E)
      6.1.2.1 BASAL-TO-TOTAL RATIO
      6.1.2.2 BASAL FLOAT 1 (deMealIns is proportional to eMealIns or Carbs)
      6.1.2.3 BASAL FLOAT 2, (deMealIns value from outside the interval)
      6.1.2.4 MEAL INSULIN FLOAT 1
      6.1.2.5 OVERVIEW OF 6.1.1.2 and 6.1.1.3
      6.1.2.6 MEAL FLOAT 2 (uses AMCorIns(i) as error)
   6.1.3 FOR MULTIPLE DOSE INJECTION (MDI) AND INHALED INSULIN:
      6.1.3.1 BASAL FLOAT 1. (not used with MDI or Inhaled Insulin)
      6.1.3.2 Basal Float 2, (The Value of dMealIns is from Outside the Interval)
      6.1.3.3 MEAL INSULIN FLOAT 1
      6.1.3.4 OVERVIEW OF 6.1.3
      6.1.3.5 MEAL INSULIN FLOAT 2, (uses AMCorIns(I) as an error term)
   6.1.4 SKIPPED BG'S
   6.1.5 A MODIFIED BOLUS CALCULATOR
   6.1.6 CHANGING THE PATIENT'S SCHEDULE
   6.2 VERSIONS USING MULTIPLE-DAYS' DATA
   6.2.1 MULTIPLE DAYS' DATA (DIGITAL ADVISOR) FOR PRACTITIONERS
      6.2.1.1 FOR PUMPS
         6.2.1.1.1 PUMP TYPE D and E
            6.2.1.1.1.1 Basal Float 1, (deMealIns is proportional to eMealIns or Carbs)
            6.2.1.1.1.2 Basal Float 2, (not used with Multiple Days' Data)
            6.2.1.1.1.3 Meal Insulin Float 1
            6.2.1.1.1.4 Overview of 6.2.1.1.1.1 and 6.2.1.1.1.3 Multiple Days' Data Type D pumps
            6.2.1.1.1.5 Meal Insulin Float 2 (uses AMCorIns as the error)
         6.2.1.1.2 PUMP TYPE C
         6.2.1.1.3 PUMP TYPE B
         6.2.1.1.4 PUMP TYPE A
      6.2.1.2 SUBCUTANEOUS MULTIPLE DOSE and INHALED INSULIN
         6.2.1.2.1 BASAL FLOAT 1
         6.2.1.2.2 MEAL INSULIN FLOAT 1
         6.2.1.2.3 MEAL INSULIN FLOAT 2 (uses AMCorIns(i) as an error)
      6.2.1.3 LIMITED DOMAIN OF deRxInsl and the SAFETY-NET FORMULA for MULTIPLE DAYS' DATA VERSIONS
         6.2.1.3.1 LIMITED DOMAIN of deRxInsl
         6.2.1.3.2 SAFETY-NET FORMULA
            6.2.1.3.2.1 For Basal Float 1
            6.2.1.3.2.2 For Meal Insulin Float 1
            6.2.1.3.2.3 For Meal Insulin Float 2 (uses AMCorIns(i) as error)
   6.2.2 AUTOMATIC MULTIPLE DAYS' DATA (DIGITAL ADVISOR)
      6.2.2.1 AUTOMATION of deRxInsl
      6.2.2.2 AUTOMATION OF deMealIns
      6.2.2.3 AUTOMATIC ROUNDING OF CIR FOR PUMP TYPE A
   6.3 NON-FLOAT ALGORITHM
7 TIME INTERVALS
   7.1 FINDING THE DAY'S LAST ENTRY

1. Suffixes and Time Indices

In the present invention, the 24 hour day is divisible into multiple time intervals. The boundaries of time intervals are numbered in the manner of: time0, time1, time2, etc. These time boundaries will be referred to generically as time(i), where "i" denotes "time index".

The Time Intervals, dt(i), are found by subtracting the consecutive time boundaries.

$$dt(i) = time(i+1) - time(i) \qquad (8)$$

Each time interval is numbered the same as its upstream time boundary as shown above. Special mention should be made of the interval surrounding midnight.

$$dt0 = 24 + time1 - Tmax \qquad (9)$$

where Tmax is the last time boundary in the day, usually Bedtime. The method of finding Tmax is set forth in a later section.

The time boundaries are generally defined by the changes in the Basal Rate (in pumps) or by average mealtimes. Practitioners often set up the patient's schedule so that the Basal Rate changes, mealtimes, BG tests, Corrective Insulin Boluses, and Meal Insulin Boluses all occur at these time boundaries. While not mandatory, this practice is preferred for use with the invention. The Basal Rates are numbered the same as time intervals, thus BR1 goes between time1 and time2.

The other parameters (besides Basal Rate) are identified with the exact time boundaries, though in practical use, the patients cannot be expected to follow such a strict schedule. Therefore, there is a need for another set of time periods (called "bins" to distinguish them from intervals), each of which envelops a time boundary. The parameters that are said to occur "at a time boundary" actually occur in a bin and are given the same index number as the time boundary enveloped by the bin. The tests and boluses can be sorted into these "Time-Boundary bins". In the case of the Multiple Days' Data Versions, this is most often handled by the downloading software of the Blood Glucose Meters and Insulin Pumps, in which a schedule of bins can be set up. In the case of the Daily Update Versions, the midpoints of the primary time intervals may be used to define the boundaries of these bins.

Note that Time-Boundary Corrective Insulin measures the insulin error in the previous interval, thus when calculating parameters for the ith interval, the insulin error is "TBCorIns(d,i+1)".

Parameters that do not follow the schedules of time intervals lack the time interval index integer. In the Multiple Days' Versions, these parameters lack any index at all.

In the Daily Update Versions, all parameters are given a day's index, "d", "d−1", etc in the manner of BF(d,i) or TDD(d).

FIG. 1 and FIG. 2 show the two pages of an exemplary Input Form for Version 6.2.1.1.1, the Multiple Days' Data Version for Pump D. FIG. 1 shows un-indexed parameters that have a single value for the Interaction. FIG. 2 shows the time intervals containing time-interval-indexed parameters.

The parameters that pertain to a unique date and time are denoted with the functional form: "parameter(t)". A few of these appear in the derivations herein for explanatory purposes, but none are used in the present invention.

2. Glossary

Average Glycemic Index (AGI): For average carbohydrates, the ratio of the grams of glucose entering the blood within two hours divided by the total grams of sugar in the carbohydrate. There are published studies for this figure. It ranges between 60% and 90%.
s
AIM Formulas: An acronym for "Accurate Insulin Management" (See Ref 1, which is incorporated by reference as if fully set forth herein). A set of statistically derived formulas used to estimate three parameters for the patient. There are three formulas. In each, a constant (beginning with "K") was determined statistically:

$$BasalAIM = Kb * TDDavg \qquad (10)$$

$$CFaim = Kcf / TDDavg \qquad (11)$$

$$CIRaim = Kcir * BodyWeight(lbs) / TDDavg \qquad (12)$$

The values of these constants change from time to time as new research is done.

The latest values (See Ref 1) are: Kb=0.48, Kcf=1700, Kcir=2.8

After-Meal Corrective Insulin: Corrective boluses taken after meals (post-prandially) in the previous day in the ith interval. (Daily Update Version)

AMCorIns(d−1,i): "After-Meal Corrective Insulin": Corrective boluses taken after meals (post-prandially) in the previous day in the ith interval. (Daily Update Version)

AMCorIns(i): "After-Meal Corrective Insulin for the ith time interval" The average of corrective boluses taken after meals (post-prandially) in the ith time interval. (Multiple Past Days Version)

Basal Rate: The rate in (insulin units/hour) at which Basal Insulin is administered.

Basal Rate Float: CIR or Meal Insulin is determined by the practitioner or by an estimation formula and BR is determined by subtracting the change in Meal Insulin (Enhanced or conventional) from the total desired change, dRxInsl (Enhanced or conventional).

Basal(d): "Basal Insulin." Basal insulin for the current day, calculated from the basal rates by the invention. (Daily Update Version)

Basal(d,i): Basal Insulin for the current day and time interval (Daily Update Version)

Basal(i): Basal for the time interval (Multiple Days' Version)

Basal: "Basal Insulin." 1. General definition: Insulin that is administered continuously by pump or insulin that is injected manually and stays in the body for a long time due to its special chemical make-up. 2. Computer variable: The current total of Basal Insulin administered during the day as calculated from the basal rates.

SUM(Basal(i)) over the day calculated by the invention. (Multiple Days' Version)

BasalTot: "Basal Insulin Total." Current Basal Insulin dose programmed into the pump at the time of the interaction with the Practitioner. Calculated by the pump. It should equal Basal. (Multiple Day's Version)

BG(i): Average of blood glucose tests over many days at approximately the same time boundary, time(i), during the day, calculated by the glucose meter's downloading software. (Multiple Day's Version)

BGmean: Overall average of blood glucose tests since last interaction or in the calendar period being analyzed, obtained from the BG meter's downloading software. (Multiple Day's Version)

BGpd: "BG's per day." The average number of BG tests per day in the calendar period being analyzed. (Multiple Day's Version)

BGsd(i): "BG standard deviation for the ith time interval" obtained from the BG meter's downloading software. (Multiple Day's Version)

BGsd: "BG standard deviation," over the calendar period being studied. Obtained from the BG meter's downloading software. (Multiple Day's Version)

BG, Blood Glucose Concentration: These tests are self-administered several times during the day, usually on the time boundaries. At the present state of the art, they are determined by placing a drop of blood on a test strip in a blood glucose meter. The meter stores the values and times in its memory. At each practitioner/patient interaction, the values are generally downloaded from the Blood Glucose Meter's memory by software that graphs the data points and calculates several values including the overall average denoted BGmean, and the time boundary averages, denoted BG(i). Some models of BG meter are able to link to insulin pumps providing a combined and integrated download of data.

Bin: A time period enveloping a Time Boundary of the primary Time Interval system. Any BG test or bolus occurring within the Bin is treated as though it occurred on the Time Boundary.

Bolus: (from the Latin, ball) Insulin infused in a short elapsed time as ordered by the patient, as distinguished from Basal Insulin, which is infused slowly, continuously and automatically either by a pre-programmed pump or by injection of a slow-acting insulin.

Bolus Time Period(i): Boluses are identified with Time Boundaries, but there is variability in the timing of them. To resolve this, a system of Bolus Time Periods is used. It has boundaries alternating in staggered fashion between the boundaries of the regular Basal Intervals such that any BG or Bolus falling in the Bolus Time period is automatically considered as occurring exactly on the regular Basal Time Boundary.

Boli(i): "Bolus Insulin": The average sum of Meal Insulin+Corrective Insulin for a time interval, so called because it is administered in boluses rather than continuously. (Multiple Past Days' Version)

BoT: "Basal over Total", Basal/TDD.

BoT(d): "Basal over Total" Basal/TDD for the day.

BoTFbk: "Basal over Total, Feedback". A parameter in the Daily Update Versions. This factor, multiplied times the day's proposed insulin change, will yield the amount of change to Basal.

BoTTgt: "Basal over Total, Target." The desired value of Basal/TDD (Daily Update Version)

BoTTgtRec: "Basal over Total, Target Recommended" Recommended value of BoTTgt (Daily Update Version)

BR(d,i): "Basal Rate" for the ith time interval." Current setting for the rate at which Basal Insulin is delivered. The rate is programmable in the pump so that it can change several times during the day. (Daily Update Version)

BR(i): "Basal Rate" for the time interval." Current setting for the rate at which Basal Insulin is delivered. The rate is programmable in the pump so that it can change several times during the day. (Multiple Days' Version)

BRavg: "Basal Rate Average", Basal/24

BRavgRec: "Basal Rate Average Recommended"

BRf: "Basal Rate, Fasting". The BR that would sustain a patient's blood glucose in the target range if no meals are consumed within 12 hours previous and if the measurement is not being made in the Late-Sleep Interval (to avoid the complications of the Pre-Dawn effect).

BRkey: The key Basal Rate. Other Basal Rates are pegged to it.

BRlateSlp: "Basal Rate in Late-Sleep time interval".

BRrec(i): "Basal Rate, Recommended for the ith time interval." Calculated by the present invention. (Multiple Past Days Version)

BRreliable: A set of basal rate data chosen for reliability, high frequency of associated BG tests, etc. Used with the Kf calculator BRrx(i): "Basal Rate, Prescription for the ith time interval." The value the Practitioner gives to the patient, after reviewing the case. (Multiple Past Days Version)

BRsimilar: A set of basal rate data chosen for similarity or closeness to the fasting basal rate. Used with the Kf calculator Carbohydrate-to-Insulin Ratio (see CIR): A personalized conversion constant; current value.

Carb-Counting: The technique of determining meal insulin by first counting the grams of carbohydrate in the meal about to be consumed and then dividing by CIR.

Carbm: "Carbohydrate grams modified"; Used in bolus calculators that incorporate exercise.

Carbs: "Grams of Carbohydrate"

CarbSh(i): "Carb Share." When used with all but pump type A, actual grams of carbohydrate or 15 gm "exchanges" are used. When used with pump type A, with no memory for MealIns(i), this parameter is the Practitioner's or Patients's estimate of the relative magnitude of carbohydrates consumed in each time interval. For pump type A any units are acceptable, because the parameter is only used as a percent of the total, CarbShTot. Example units: grams of carbohydrate (preferred), percent of the total, units of meal insulin (if CIR constant). (Multiple Days' Version)

CarbShTot: "Carb ShareTotal"; calculated as CarbShTot=sum(CarbSh(i))

CF: "Correction Factor." A personalized factor used to calculate Correction Boluses. See CorBol(t) and AIM Change to: as in "Change to Pescription Insulin", "Change to Basal Insulin", "Change to Enhanced Meal Insulin". This phrase denotes a proposed change in the named quantity, from the last measured value to the recommended value. For the Daily Update version, this is the change from one day to the next. For the Multiple Days' Data Version this is the change from the average over the past calendar period to the recommended value. Digital variables denoting changes are preceeded by a lower-case "d" as in calculus.

CIR(d,i): "Carbohydrate-to-Insulin Ratio" The CIR for a time interval dt(i) in the current day. (Daily Update Version)

CIR(i): "Carbohydrate-to-Insulin Ratio" The CIR for a time interval dt(i). (Multiple Past Days Version)

CIR: "Carbohydrate-to-Insulin Ratio". A personalized conversion constant; current value.

$$\text{CIR=(weight of carbohydrates consumed)/(insulin required to metabolize the carbohydrates)} \qquad (13)$$

See MealBol(t), and AIM. Calculation of this parameter is one of the chief goals of PumpMaster. (Multiple Past Days Version)

CIRrec(i):"Carbohydrate-to-Insulin Ratio, recommended for a time interval" (Multiple Past Days' Version)

CIRrec:"Carbohydrate-to-Insulin Ratio, recommended" (Multiple Past Days Version)

CorBol(t): "Corrective Bolus at a unique date and time." The patient periodically tests his/her Blood Glucose concentration. If it is too high, the patient calculates a bolus of insulin by the formula:

$$\text{CorBol}(t)=(\text{BG}(t)-\text{Target})/\text{CF} \qquad (14)$$

Where Target is the desired BG level and CF is a personalized Correction Factor.

CorIns(i): "Corrective Insulin." The sum of CorBol(t) at all times within the interval, including "After-Meal" and "Time-Boundary" times. (Multiple Past Days' Version)

CorIns(d,i) "Corrective Insulin." The sum of CorBol(t) at all times within the interval including "After-Meal" and "Time-Boundary" times during the current day. (Daily Update Version)

CorTot(d): "Corrective Insulin Total." The sum of corrective insulin at all times within the current day. (Daily Update Version)

CorTot: "Corrective Insulin Total." The average of the sum of corrective insulin at all times within day. (Multiple Past Day's Version)

dBasalAuto: The automated version of dBasal. (Automatic Multiple Days' Version)

dBaslToAIM: The change in Basal necessary to achieve the BasalAIM value deMealIns(d,i): "Change in Enhanced Meal Insulin" for the time interval for the current day. (Daily Update Version)

deMealIns(i): "Change in Enhanced Meal Insulin" for the time interval. (Multiple Past Days Version)

deMealIns: "Change in Total Enhanced Meal Insulin." For the whole day. (Multiple Past Days' Version)

deMealInsAuto: The automated version of dEmealIns. (Automatic Multiple Days'Version)

deRxInsAuto: "Change in Enhanced Prescription Insulin, Automatic"; estimated automatically. (Automatic Multiple Days' Version)

deRxInsl(d,i): "change in Enhanced Prescription Insulin in a time interval of the current day" (Daily Update Version)

deRxInsl(i): "change in Enhanced Prescription Insulin in a time interval" (Multiple Past Days Version)

deRxInsl: "change in Total Day's Enhanced Prescription Insulin" (Multiple Past Days Version)

deRxInslld(i): "change in Enhanced Prescription Insulin, large domain in the interval" The "Safety-Net" formula. One of two formulas for deRxInsl(i). (Multiple Days' Version)

deRxInslsd(i): "change in Total Enhanced Prescription Insulin, small domain"; One of two formulas for deRxInsl(i) for "Safety-Net" purposes. (Multiple Days' Version)

dt(i): "difference in time"; The length of the "ith" time interval

Early-Sleep Time Interval: The time interval starting with Bedtime and ending with the Mid-Sleep time boundary. Most diabetic patients are encouraged not to snack at bedtime and to take a mid-sleep BG at about 3:00 AM. If this advice is followed, then the Early Sleep Time Interval gives a good indication of the true "inactive basal rate", BRf, that underlies many other time intervals.

eMealIns(d,i): "Enhanced Meal Insulin for the time interval." The sum of the Meal Boluses plus the After-Meal Corrective Boluses during time interval dt(i) for the current day. (Daily Update Version)

eMealIns(i): "Enhanced Meal Insulin for the time interval." A multiple-day average of the sum of After-Meal Insulin plus Time-Boundary Corrective Insulin in a time interval. (Multiple Past Days Version)

eMealInsRec(d,i): "Enhanced Meal Insulin Recommended for the current day and time interval". (Daily Update Version)

eMealInsRec(i): "Enhanced Meal Insulin for the time interval, recommended". Calculated by the invention. (Multiple Past Days Version)

eMealInsTot(d): "Enhanced Meal Insulin Total for the current day" The sum of eMealIns(i) during the current day. (Daily Update Version)

eMealInsTot: "Enhanced Meal Insulin Total." The sum of MealIns(i) plus the sum of After-Meal Corrective Insulin during the whole day averaged over several days. (Multiple Days' Version)

Enhanced: A word used to describe a certain modified variable system, in which After-Meal Corrective Insulin is incorporated as part of Meal Insulin.

eRxInsl: "Total Day's Enhanced Prescription Insulin." A subset of TDD, defined as: The sum of Enhanced Meal Insulin+Basal Insulin during the day. It is usually "Prescription" by the practitioner. The invention proposes methods of calculating it automatically.

ExerCarbs: "Exercise Carbs." The equivalent of exercise in grams of carbohydrate.

FInsAuto: A multiplier that limits dRxInsAuto. (Automatic Multiple Days' Version)

Fixed-Meal: Another simpler technique of determining meal insulin other than carb-counting. It involves eating meals of fixed menu preceded by fixed amounts of insulin.

Float: An algorithm in which the change to one of the two main parameters, EmealIns or BR is estimated or determined by the practitioner, and the change to the other parameter is determined by subtracting the estimated insulin change from the total desired change in insulin. The "floated" parameter is the one that is determined by subtraction.

GlycemicIndex: The ratio of calories available from carbohydrates within 2 hours after consumption to total calories in the carbs. It is different for different types of carbs.

Interaction: "Patient/practitioner Interaction." An inclusive term, including person-to-person interactions, and telecommunication-based interactions in which the patient's parameters are re-adjusted.

Interval: The day is divided into time intervals for the purpose of enabling a patient's insulin dosing to be varied throughout the day and analyzed on a time-dependent basis. The intervals usually are bounded at the times of the Basal Rate changes.

Kb: A statistically-derived constant used in the formula for estimated Basal. The latest publication of the "AIM" formulas give the latest value of Kb=0.48 (Ref 1). It is used in the formula:

$$Basal=Kb*TDDavg \tag{15}$$

Kcf: A statistically-derived constant used in the formula for estimated CF. The latest publication of the "AIM" formulas (Ref 1) give the latest value of Kcir=1700. It is used in the formula:

$$CF=Kcf/TDDavg \tag{16}$$

Kcir: A statistically-derived constant used in the formula for estimated CIR. The latest publication of the "AIM" formulas (Ref 1) give the latest value of Kcir=2.8. It is used in the formula:

$$CIR=Kcir*BodyWeight/TDDavg \tag{17}$$

KcirW: A constant used in the formula for estimated CIR. The latest publication (Ref 1) give the latest value of Kcir=500. It is used in the formula:

$$CIR=KcirW/TDDavg \tag{18}$$

Kcycle: A constant representing the fraction by which CorTot is intended to be reduced in a specified number of days (Ncycle). (Daily Update Version)

Keyb: as in "Key Basal Rate", An identifier for an interval that is considered to have dependable data and whose BR is also used in other intervals.

Keyc: as in "Key CIR", An identifier for an interval that is considered to have dependable data and whose CIR is also used in other intervals.

Kf="K fasting"; A constant <1. The ratio of fasting basal rate to a chosen "reliable" basal rate $$Kf=BRf/BRreliable \tag{19}$$

Kmauto: "K meals,auto"; a positive constant <=1 whose purpose is determining deMealIns. (Automatic Multiple Days' Version)

Kfbk: "K Feedback", A constant in the formula for BoTFbk that adjusts the speed of convergence (days) of the Basal-to-Total Ratio to a target value. (Daily Update Version)

KrxInsl: a positive constant <=1 whose purpose is limiting dRxInsl. (Daily Update Version)

KrxInslMax: The maximum allowable value of deRxInsl/TBCorTot (Multiple Days' Version)

Late-Sleep Time Interval: (same as Pre-Dawn Time Inteval) The time interval starting with the Mid Sleep time boundary and ending with the Breakfast time boundary. This time interval is characterized by the "Pre-Dawn Effect", which is a need for somewhat more insulin that would be normally expected. It is believed that this effect is linked to a release of growth hormone. This time interval is the most dependably carb-free of all the intervals. It would be the best candidate for the "inactive fasting basal rate" were it not for the Pre-Dawn Effect.

Meal Insulin: Insulin taken in a "bolus" concurrently or just before consumption of carbohydrates.

Meal Insulin Float: BR is determined by the practitioner or by an estimation formula, and Meal Insulin (enhanced or conventional) is determined by subtracting the change in Basal from the total desired change, dRxInsl (Enhanced or conventional). Then change in CIR is determined from the change in Meal Insulin (enhanced or conventional). Use of this type of Float allows the Basal Rates to be kept more uniform. This is a benefit if a patient skips a meal.

MealBol(t): "Meal Bolus at a unique date and time." When eating, a patient calculates the grams of carbohydrates being consumed and calculates an insulin bolus by the following formula:

$$\text{MealBol}(t) = (\text{gm of carbohydrate})/\text{CIR} \quad (20)$$

where CIR is the personalized Carbohydrate-to-Insulin Ratio

MealIns(d,i)=Meal insulin within a time interval (Daily Update Version)

MealIns(i)=Meal insulin within a time interval (Multiple Past Day's Version)

MealInsTot=The total of meal insulin in a day

NBGs(i): "number of BG's in the time interval" over the calendar period being analyzed. (Multiple Day's Version)

NBGs: "number of BG's." Total number of BG tests in the BG meter since last download or in the calendar period being analyzed. (Multiple Day's Version)

Ncycle: the number of days until a fraction Kcycle of the insulin error is removed. (Daily Update Version)

NDbg: "number of days of blood glucose." Number of days of BG tests in the calendar period being analyzed. (Multiple Day's Version)

Peg: (verb) To set a parameter (CIR or BR) in one interval equal to a constant times the same parameter in another interval. The parameter is said to be "pegged" to the key interval. Normally the constant is equal to the ratio of the parameters on day of adjustment by the Practitioner, so that the same ratio is maintained in the future.

Pen: A pocket-portable insulin delivery device, named for its resemblance to a writing implement.

PmPctBGsd: The database "population" mean of the quantity (BGsd/BGmean), used in the automation of deRxInsl. (Automatic Multiple Days' Version)

Practitioner: The physician or nurse who analyzes a diabetic patient's parameters and prescribes insulin dose regimen.

Pre-Dawn Time Interval: (same as Late-Sleep Time Interval)

PsdPctBGsd: The database "population" standard deviation of the quantity (BGsd/BGmean), used in the automation of deRxInsl. (Automatic Multiple Days' Version)

Reliable data set: A special use of the word to indicate an interval or set of data that has good statistics on a certain parameter, i.e. high frequency of BG testing, low Standard Deviation.

RxInsl: "Total Day's Prescription Insulin." A subset of TDD, defined as: The sum of Meal Insulin+Basal Insulin during the day. It is prescribed by the practitioner, unlike Corrective Insulin.

Similar data set: A special use of the word indicating that the data set is likely to have a parameter of a value close to one being sought statistically.

Swtch: "Switching parameter"; A two valued parameter whose purpose is to evaluate deRxInsl relative to some domain limits and shift between the two "domain" equations for deRxInsl(i). (Multiple Days' Version)

Target: General: A number used in a feedback algorithm representing the desired result.

TargetAM: "Target Blood Glucose After Meals". Corrective insulin is calculated according to how high a patient's BG is above the TargetAM. See CorBol TargetTB: "Target Blood Glucose Before Meals". Corrective insulin is calculated according to how high a patient's BG is above the TargetTB. See CorBol Target Basal-to-Total Ratio: The desired value of daily Basal Insulin divided by Total Daily Insulin. Used in a feedback algorithm.

TBCorIns(d−1,i+1): "Time-Boundary Corrective Insulin." The patient is usually instructed to test his or her BG at the time boundaries. This parameter is the previous day's total of Corrective Insulin taken on or near the time boundary, time(i+1). (Daily Update Version)

TBCorIns(i+1): "Time-Boundary Corrective Insulin in the (i+1)th time interval." The patient is usually instructed to test his or her BG at the time boundaries. This parameter is the average over several days of the total of Corrective Insulin taken on or near a time boundary, time(i+1). (Multiple Past Days Version)

TBCorTot(d): "Time-Boundary Corrective Insulin Total for the current day". (Daily Update Version)

TBCorTot: "Time-Boundary Corrective Insulin Total": The sum of TBCorIns(i) over the whole day. (Multiple Past Days Version)

TDD(d−1): "Total Daily Dose" of insulin. The total amount of insulin a patient received during the previous day. (Daily Update Version)

TDDavg: "Total Daily Dose of Insulin, average." The average of TDD for several days. (Multiple Past Days Version)

Time(i): The "ith" time boundary

Time-Boundary Corrective Insulin: Corrective Insulin Boluses taken at or near a boundary of a time interval. Typically a BG test is taken at the time boundary (just before eating if the next interval is a meal interval) and the corrective bolus is calculated from this BG test.

TimeLabel(i): A short text phrase labeling each time boundary. PumpMaster offers several standard entries: Mid-Sleep, Pre-Breakfast, Pre-Lunch, Pre-Supper, Bedtime, Snack, and Basal Rate Change.

Tmax: The last time boundary of a patient's day. Usually bedtime.

3. Generic Derivations

3.1 Making Changes in the Carbohdrate-to-Insulin Ratio, CIR:

We can re-arrange the definition of CIR in two different ways, one for current conditions and one as a recommendation, assuming that the carbohydrates do not change:

$$\text{Carbs} = \text{CIR} * \text{Meal Insulin} \tag{21}$$

$$\text{CIRrec} = \text{Carbs}/\text{Recommended Meal Insulin} \tag{22}$$

If Meal Insulin or Carbs are not known, then differential methods can be employed:

$$\text{CIRrec} = \text{CIR} + \text{dCIR} \tag{23}$$

We need the derivative of CIR with respect to Meal Insulin to use in the formulas below (the derivative is in parentheses):

$$\text{dCIR} = (\text{dCIR}/\text{dMeal Insulin}) * \text{dMeal Insulin} \tag{24}$$

And $$\text{dMeal Insulin} = \text{dCIR}/(\text{dCIR}/\text{dMeal Insulin}) \tag{25}$$

The following derivation leads to the formula for calculating dCIR, the change in CIR, that will produce a change d(Meal Insulin) in Meal Insulin. There are several ways to calculate or estimate the derivative. To obtain them, start with the definition of CIR:

$$\text{CIR} = \text{Carbs}/(\text{Meal Insulin}) \tag{26}$$

Differentiate using calculus:

$$(\text{dCIR}/\text{dMeal Insulin}) = -\text{Carbs}/(\text{Meal Insulin})^2 \tag{27}$$

Substitute equation (21) into equation (27) to obtain:

$$(\text{dCIR}/\text{dMeal Insulin}) = -\text{CIR}/(\text{Meal Insulin}) \tag{28}$$

This is an estimate of the derivative that depends on CIR. It is possible to eliminate CIR from the equation by substituting a correlation from a statistical study. For example, the AIM correlation, (Ref 1) is used below. It says:

$$\text{CIR} = \text{Kcir} * \text{BodyWt}/\text{TDDavg} \tag{29}$$

where Kcir is a statistically-determined constant.

Substitute this into equation (28) for CIR to obtain the following generic equation:

$$(\text{dCIR}/\text{dMeal Insulin}) = -(\text{Kcir} * \text{BodyWt}/\text{TDDavg})/(\text{Meal Insulin}) \tag{30}$$

If Meal Insulin is unavailable, it can be calculated as:

$$\text{Meal Insulin} = \text{TDDavg} - \text{Basal} - \text{Corrective Insulin} \tag{31}$$

Leading to:

$$(\text{dCIR}/\text{dMeal Insulin}) = -(\text{Kcir} * \text{BodyWt}/\text{TDDavg})/(\text{TDDavg} - \text{Basal} - \text{Corrective Insulin}) \tag{32}$$

The AIM statistical studies show that Basal is slightly less than half of TDDavg. Corrective Insulin is usually small, so we can say that Meal Insulin is approximately half of TDDavg. This leads from equation (30) to the equation:

$$(\text{dCIR}/\text{dMeal Insulin}) = -(\text{Kcir} * \text{BodyWt} * 2/\text{TDDavg}^2) \tag{33}$$

and finally:

$$\text{dCIR} = -(\text{Kcir} * \text{BodyWt} * 2/\text{TDDavg}^2) * \text{dMeal Insulin} \tag{34}$$

Another correlation (Ref 2) estimates $\text{CIR} = \text{Kcirw}/\text{TDD}$. By similar steps this leads to:

$$\text{dCIR} = -(\text{Kcirw} * 2/\text{TDDavg}^2) * \text{dMeal Insulin} \tag{35}$$

The change in Meal Insulin, dMealIns, may be obtained as follows:

$$\text{dMealIns} = \text{MealInsNew} - \text{MealInsOld} \tag{36}$$

$$\text{dMealIns} = \text{Carbs} * (1/\text{CIRnew} - 1/\text{CIRold}) \tag{37}$$

or it may be input by the Practitioner.

3.2 Some Important Equations:

3.2.1 Conventional Insulin Nomenclature

The earlier section showing the different types of insulin is re-written below using the variable names.

Recall the definitions: RxInsl: Prescription Insulin,
TBCorTot: Total Day's Time-Boundary Corrective Insulin,
AMCorTot: Total Day's After-Meal Corrective Insulin
CorTot: Total Day's Corrective Insulin $$\text{TDD} = \text{RxInsl} + \text{CorTot} \tag{38}$$

Where $\text{RxInsl} = \text{Basal} + \text{MealIns}$ (39)

For small changes:

$$\text{dRxInsl} = \text{dBasal} + \text{dMealIns} \tag{40}$$

Within a time interval, similar equations holds true:

$$\text{RxInsl}(i) = \text{Basal}(i) + \text{MealIns}(i) \tag{41}$$

$$\text{dRxInsl}(i) = \text{dBasal}(i) + \text{dMealIns}(i) \tag{42}$$

The present invention incorporates the following concept: The Total Day's Corrective Insulin, CorTot represents an "error" in the patient's Prescription Insulin; the goal is CorTot=0. The practitioner (or an automatic algorithm) decides how much of CorTot to eliminate. This amount is called dRxInsl mimicking the words "Change in Total Prescription Insulin". By making this change, the program can indirectly cause CorTot to be reduced in the days ahead. dRxInsl may be determined differently, depending on the Version:

Daily Update Version: KrxInsl is a pre-determined constant <=1. It is used to set dRxInsl in the manner shown below:

$$\text{dMealIns} + \text{dBasal} = \text{dRxInsl} = \text{KrxInsl} * \text{CorTot} \tag{43}$$

Similarly, in the time interval:

$$\text{dMealIns}(i) + \text{dBasal}(i) = \text{dRxInsl}(i) = \text{KrxInsl} * \text{CorIns}(i+1) \tag{44}$$

At the present time KrxInsl=0.16 for the Daily Update algorithms, but the value of KrxInsl is subject to adjustment for optimum safety and performance.

Multiple Days' Data Version: In the Manual Sub-Version, dRxInsl is input by the Practitioner for each Patient/Practitioner Interaction. Any value is allowed up to a maximum of KrxInslMax*CorTot, where KrxInslMax is a fractional constant:

$$\text{dMealIns} + \text{dBasal} = \text{dRxInsl} <= \text{KrxInslMax} * \text{CorTot} \tag{45}$$

Each time interval gets its share of the "fix" in proportion to its share of the total error:

$$\text{dMealIns}(i) + \text{dBasal}(i) = \text{dRxInsl}(i) = \text{dRxInsl} * (\text{CorIns}(i+1)/\text{CorTot}) \tag{46}$$

At the present time, KrxInslMax=0.5 but is subject to adjustment for optimum safety and performance.

In the automatic Sub-version, an automatic method determines dRxInsl (explained in the section entitled "Automatic Multiple Days' Data (Digital Advisor)".

The left-hand-side of equation (44) or (46) is implemented for the interval in one of two ways. These are given the name "floats":

The MealIns Float: dBasal($i$) is estimated first; then the invention calculates dMealIns($i$)=dRxInsl($i$)−dBasal($i$). Some of the ways for estimating dBasal($I$) are:

Borrowing new Basal Rate from another interval;
Estimating Basal Rate from another algorithm (e.g. a Basal Float);
Estimating dBasal(i) from the carb-free latter part of a time interval using TBCorIns(i) as the error indicator. The float is done on the first part of the interval, using AMCorIns(i) as the error. (47)

or

The Basal Float: dMealIns($i$) is estimated first; then the invention calculates dBasal($i$)=dRxInsl($i$)−dMealIns($i$). Some of the ways for estimating dMealIns($i$) are:

Borrowing MealIns(i) or CIR(i) from another interval;
Estimating dMealIns(i) as a share of day's total dMealIns in the same proportion as CarbSh(i)/CarbShTot;
Estimating dMealIns(i) as a share of day's total dMealIns in the same proportion as MealIns(i)/MealInsTot (48)

3.2.2 Enhanced Insulin Nomenclature:

The types of insulin-delivery systems that incorporate Insulin-on-board calculations make it safer for the patient to use After-Meal Corrective Insulin dosing, (variable name: AMCorIns) It is called "corrective" because it uses the correction formula, equation (14). However, since it is part of the insulin needed to cope with a specific meal of carbs, it is more convenient to lump it together with Meal Insulin by defining new variables:

Enhanced Meal Insulin: eMealIns=MealIns+AMCorIns
Enhanced Prescription Insulin: eRxInsl=Basal+eMealIns
This is explained better as follows:

$$TDD = eRxInsl + TBCorIns \quad (49)$$

$$\text{where } eRxInsl = Basal + eMealIns \quad (50)$$

$$\text{and } eMealIns = MealIns + AMCorIns \quad (51)$$

The two quantities in eMealIns are added together at the start of these calculations and treated as a single variable. For small changes:

$$deRxInsl = dBasal + deMealIns \quad (52)$$

Within a time interval, similar equations holds true:

$$eRxInsl(i) = Basal(i) + eMealIns(i) \quad (53)$$

$$deRxInsl(i) = dBasal(i) + deMealIns(i) \quad (54)$$

The present invention incorporates the following concept: The Total Time-Boundary Corrective Insulin, TBCorTot represents an "error" in the patient's Enhanced Prescription Insulin; the goal is TBCorTot=0. The practitioner (or an automatic algorithm) decides how much of TBCorTot to eliminate. This amount is called deRxInsl mimicking the words "Change in Total Enhanced Prescription Insulin". By making this change, the program can indirectly cause TBCorTot to be reduced in the days ahead. deRxInsl may be determined differently, depending on the Version:

Daily Update Version: KrxInsl is a pre-determined constant <=1. It is used to set deRxInsl in the manner shown below:

$$deMealIns + dBasal = deRxInsl = KrxInsl*TBCorTot \quad (55)$$

Similarly, in the time interval:

$$deMealIns(i) + dBasal(i) = deRxInsl(i) = KrxInsl*TBCorIns(i+1) \quad (56)$$

At the present time KrxInsl=0.16 for the Daily Update algorithms, but the value of KrxInsl is subject to adjustment for optimum safety and performance.

Multiple Days' Data Version: In the Manual Sub-Version, deRxInsl is input by the Practitioner for each Patient/Practitioner Interaction. Any value is allowed up to a maximum of KrxInslMax*TBCorTot, where KrxInslMax is a fractional constant <=1.

$$deMealIns + dBasal = deRxInsl <= KrxInslMax*TBCorTot \quad (57)$$

Each time interval gets its share of the "fix" in proportion to its error:

$$deMealIns(i) + dBasal(i) = deRxInsl(i) = deRxInsl*(TBCorIns(i+1)/TBCorTot) \quad (58)$$

At the present time KrxInslMax=0.5 but is subject to adjustment for optimum safety and performance. In the automatic Sub-version, an automatic method determines deRxInsl (explained "Automatic Digital Assistant").

The left-hand-side of equation (56) or (58) is implemented for the interval in one of two ways. These are given the name "floats":

The MealIns Float: dBasal($i$) is estimated first; then the invention calculates deMealIns($i$)=deRxInsl($i$)−dBasal($i$). Some of the ways for estimating dBasal($i$) are:

Borrowing Basal(i) from another interval
Estimating Basal(i) from another algorithm (e.g. a Basal Float) (59)

or

The Basal Float: deMealIns is estimated first; then the invention calculates dBasal($i$)=deRxInsl($i$)−deMealIns($i$) Some of the ways for estimating deMealIns are:

Borrowing eMealIns(i) or CIR(i) from another interval
Estimating deMealIns(i) as a share of day's total deMealIns in the same proportion as CarbSh(i)/CarbShTot. (60)
Estimating deMealIns(i) as a share of day's total deMealIns in the same proportion as eMealIns(i)/eMealInsTot 3.2.3 General For a given Version, the different time intervals may have different types of float.

The Basal float has the advantage that it can be used for all time intervals in the day, enabling easy changes to the patient's daily routine.

The Meal Insulin Float has the advantage that Basal Rate schedule can be kept simple, and changes in eating habits can be handled by CIR which addresses the changes only if the person consumes carbs and takes a meal bolus. However, since the Meal Insulin Float can only affect the time intervals with meals in them, the Basal Float equations must still be used for the non-meal intervals.

3.3 The Two-Level Basal System, and the Kf Calculator

Some Practitioners prefer a "Two Level Basal" schedule, that assigns a single Basal Rate, BRf, (for BR fasting) around the clock except for the Late-Sleep time interval, just before waking. The Late-Sleep interval is different because of the "Pre-Dawn Phenomenon", which is the requirement for somewhat more insulin during the second half of the sleep period. This results in the two-levels of Basal Rate: BRf and BRlateSlp. Finding BRf becomes an important task.

A non-meal interval would be best for determining BRf. Typically, the non-meal intervals are the Early-Sleep and Late-Sleep intervals. However, neither of these is a perfect candidate:

The Early-Sleep interval, if truly meal-free, would give the best value of BRf, but often patients "cheat" by taking a bedtime snack. Also, the patient must interrupt his or her sleep in order to take the necessary mid-sleep BG test, so the data is often not available. The Late-Sleep or pre-dawn interval is the most readily available and most often meal-free, but this interval is unsuitable because of the "dawn phenomenon". Neither of these is a perfect candidate for BRf.

The present invention incorporates two generalized methods that are designed to provide several ways to calculate BRf. Some nomenclature should be explained: BRf is intended to be used in most intervals excluding a few which are called "excluded intervals". One interval or category of BR's with good statistical reliability may be nominated as a "reliable" interval (with basal rate BRreliable). Another interval or data set may be nominated as a "similar" interval because its basal rate, BRsimilar, is similar to BRf. The present invention uses two generic methods to obtain BRf.

4.3.1 Statistical Correlation:

BRf may be obtained by a familiar least squares formula that statistically correlates paired values of "reliable" and "similar" data over the recent calendar period with a correlation constant, Kf, estimated to fit the formula BRsimilar=Kf*BRreliable.

$$Kf=SUM[(BRsimilar)*(BRreliable)]/SUM[BRreliable^2] \quad (61)$$

Once calculated, the correlation constant, Kf, is used to convert the values of the "reliable" basal rates into values of BRf until the next Practitioner interaction:

$$BRf=BRreliable*Kf \quad (62)$$

3.3.2 Averaging:

BRf may be obtained by averaging certain sets of BRsimilar data from the same day or the previous day (in the case of the Daily Update Version), or from the recent calendar period (in the case of the Multiple Days' Data Version). The smoothing effect of the averaging process helps to produce good values.

Some particular applications of these two methods are described below:

The the Early-Sleep BR's of nights in which there was no bedtime snack are used as BRsimilar. Paired with these are values of Late Sleep BR immediately following, in the early morning of the next calendar day, which are used as BRreliable. The formula for subsequent use is:

$$BRf=Kf*BRlateSlp \quad (63)$$

The average of BR's except BRlateSlp may be nominated as the similar data set, paired with BRlateSlp as the reliable data set. The resulting formula appears the same, as equation (63) though the Kf is different.

The average of all BR's except BRlateSlp may be used directly as BRf.

The average of all BR's i.e. (Basal/24) may be used directly as BRf.

The average of all BR's i.e. (Basal/24) may be nominated as the similar data set, paired with BRlateSlp as the reliable data set. Once again the resulting formula is the same as equation (63).

The Early-Sleep BR's of nights in which there was no bedtime snack are used as BRsimilar. Paired with these are "reliable" values of Basal/24. The formula for subsequent use is:

$$BRf=Kf*Basal/24 \quad (64)$$

The average of BR's except BRlateSlp may be nominated as the similar data set, paired with the average of all BG's, i.e. Basal/24 as the reliable data set. The resulting formula is the same as (64) but Kf is different.

The average of the Basal Float 1 results for all the other intervals (except Late-Sleep interval) may be nominated as the similar data set, paired with BRlateSlp as the reliable data set. Once again the resulting formula looks the same as equation (63)

The average of the Basal Float 2 results for all the other intervals (except Late-Sleep interval) may be nominated as the similar data set, paired with BRlateSlp as the reliable data set. Once again the resulting formula looks the same as equation (63)

The average of the Meal Insulin Float 2 results for all the other intervals (except Late-Sleep interval) may be nominated as the similar data set, paired with BRlateSlp as the reliable data set. Once again the resulting formula looks the same as equation (63)

Additional applications of this type are mentioned throughout the text that follows.

General Discussion of Kf:

The Kf Calculator is particularly well-suited for the Multiple Days' Data Versions so that it will be performed external to the insulin-delivery device. It is designed to be operated by the Practitioner at the time of a patient/practitioner interaction. This is because it depends upon digital memory of a sufficient number of nights to obtain enough data points to calculate an accurate value for Kf.

4. Types of Insulin Delivery Systems

The following is a list of insulin delivery systems showing the Versions of the present invention applicable to each:

Type A pumps: Have memory for TDD for several days. They have memory of the programmed Basal schedule, Basal(i). They have no memory for CF, CIR, CIR(i), BG(i), MealBol(t), MealIns(i), TBCorIns, AMCorIns, CorBol(t), or CorIns(i). Therefore, average combined boluses for the day must be obtained by subtracting Basal from TDDavg. Example: Medtronic MiniMed Paradigm 511.

Version 6.2.1.1.4: which uses Multiple Days' Accumulated Data. Program is external to pump.

Type B pumps: In addition to the Type A memories, these have BG(i), actual carbs for CarbSh(i); CIR(i), CF, and Combined Boluses, Boli(i). Examples: Medtronic MiniMed Paradigm 512 and 712.

Version 6.2.1.1.3: which uses Multiple Days' Data. Program external to pump.

Type C pumps: In addition to other Type B memories, these have memories for MealIns(i) and CorIns(i). Example: Deltec Cozmo.

Version 6.2.1.1.2: which uses Multiple Day's Data. Program external to pump.

Type D pumps: In addition to Type C memories, these pumps have, as a minimum, memories for AMCorIns(i) and TBCorIns(i).

Versions 6.2.1.1.1: which uses Multiple Days' Data. Program external to pump.

Type E pumps: Have all the parameters of the Type D pumps as a minimum and have the program installed internally.

Versions 6.1.2: which uses automatic Daily Update. Program internal to pump.

Version 6.2.1.1.1: which uses Multiple Days' Accumulated Data. Program external to pump.

Subcutaneous or Inhaled Insulin Delivery in which the insulin delivery device and the BG meter clip together into a kit or otherwise communicate with each other so that data is recorded digitally.

Versions 6.1.3: which uses automatic Daily Update. Program internal to the kit.

Version 6.2.1.2: which uses Multiple Days' Accumulated Data. Program external to the kit.

For the purpose of ease of presentation, these are re-organized in the Table of Contents. The different types of algorithm are shown as well:

5. Description by, Version, Embodiment, Algorithm 5.1. Versions using Daily Update:
5.1.1 Preliminary Derivations.
5.1.1.1 Time Intervals and Corrective Insulin The index "d" denotes the present day.

The index "i" denotes the "ith" time boundary or time interval (following the time boundary).

The Time-Boundary Corrective Insulin, TBCorIns(d,i) is the sum of corrective boluses occurring at the beginning of the ith interval. Each bolus needs to be identified as a Time-Boundary bolus, and it needs to be identified with the ith interval. This may be accomplished by a suitable combination of the following methods:
- identified with the ith interval if it falls between the midpoint of the previous interval and the midpoint of the ith interval.
- identified as a Time-Boundary Corrective bolus if it comes before the Meal Bolus with the same index number.
- one or both of these identifications input by the patient at bolus-time, using the controls on the insulin-delivery device.

The After-Meal Corrective insulin AMCorIns(d,i) is the sum of corrective boluses, identified by a suitable combination of the following methods:
- identified with the ith interval if it falls within the ith interval.
- identified as an After-Meal Corrective bolus by the fact of coming after the Meal Bolus for the meal that marks the start of the interval.
- one or both of these identifications input by the patient at bolus-time, using the controls on the insulin-delivery device.

5.1.1.2 KrxInsl: Governs the Size of Insulin Changes

Suppose the operation of the invention is analyzed starting at an arbitrary starting time, when TBCorTot=TBCorTotStart. This represents an error to the invention. The purpose is to decrease each day's "error", TBCorTot, by a fractional amount KrxInsl*TBCorTot, where KrxInsl <=1. This means that, starting with a "starting error", TBCorTotStart, the error should decrease in a geometric sequence. After a number of days, Ncycle, The remaining error, $$TBCorTot(Ncycle)=TBCorTotStart*[1-KrxInsl]^{Ncycle} \quad (65)$$

This remaining error approaches near-zero as Ncycle increases. The phrase "near-zero" can be defined by setting a reasonably small number for a Percent Remaining Error.

$$\text{Percent Remaining Error}=[1-KrxInsl]^{Ncycle} \quad (66)$$

For a suitable combination of Percent Remaining Error and Ncycle, the equation can be solved for KrxInsl. This is done by the invention as follows:

$$KrxInsl=1-(\text{Percent Remaining Error})^{(1/Ncycle)} \quad (67)$$

The Percent Remaining Error is set by the inventors but is subject to change. (A typical value is 10%). The choice of Ncycle is left to the practitioner. (A typical value is 14 days). This example leads to an exemplary value of KrxInsl=0.16. In plain language, "A choice of 0.16 for KrxInsl eliminates 90% of the error in two weeks." It is used in the Daily Update algorithms as follows:

$$deRxInsl=KrxInsl*TBCorTot \quad (68)$$

or $$dRxInsl=KrxInsl*TBCorTot \quad (69)$$

In the interval:

$$deRxInsl(i)=KrxInsl*TBCorIns(i+1) \quad (70)$$

or $$dRxInsl(i)=KrxInsl*TBCorIns(i+1) \quad (71)$$

5.1.2 For Pumps (Type E)
5.1.2.1 Basal-to-Total Ratio:

The Basal(d)/TDD(d) ratio is called BoT(d) for "Basal over TDD". It is calculated every day. It has been determined by medical studies that certain ratios of Basal(d)/TDD(d) lead to better management of diabetes. a target for Basal(d)/TDD(d) ratio can be set into the program by the patient or practitioner. It is called BoTTgt for "Basal over TDD, Target".

The invention contains a feedback factor to bring BoT(d) to BoTTgt. The feedback factor incorporates a constant Kfbk to regulate the speed of convergence:

$$BoTFbk(d)=BoT(d)+Kfbk*(BoTTgt-BoT(d))*\text{sign}(deRxInsl) \quad (72)$$

Where the resulting value is not allowed to be less than zero or greater than one.

This factor, multiplied times the day's proposed total insulin change will yield the amount of change to Basal. The "sign" function ensures that the magnitude of the change is correct for the "direction" of the change. The constant Kfbk is adjusted to achieve the optimum speed of convergence to BoTTgt. The feedback factor is applied as follows:

$$dBasal=BoTFbk(d)*deRxInsl \quad (73)$$

$$deMealIns=(1-BoTFbk(d))*deRxInsl \quad (74)$$

The invention provides a recommendation for BoTTgt, named BoTTgtRec, which is calculated as follows:

BoTTgtRec=1-4*CarbShTot*(Average Glycemic Index)/(a statistical correlation for caloric intake as a function of height, weight, and other easily known patient parameters)

This formula changes carbs to calories by use of the conversion factor 4, then multiplies by glycemic index to obtain the immediately-available calories from the carbs, then divides by the patient's caloric intake as estimated by body conformation. This gives the requirement for MealIns/TDD. Basal to Total ratio is one minus this quantity.

The present versions of the invention generally do not use this concept for both dBasal and deMealIns in the same time interval, but instead use one of them and determine the other parameter by subtraction from the total, deRxInsl in the manner described in the definition of "Float".

5.1.2.1 Basal Float 1, (deMealIns is Proportional to eMealIns or Carbs)

This algorithm estimates Meal Insulin using the feedback factor, BoTFbk(d). The Enhanced insulin nomenclature system is used. The total change in Enhanced Meal Insulin is taken from equations (70) and (74):

$$\text{deMealIns}(d) = \text{KrxInsl}*(1-\text{BoTFbk}(d-1))*\text{TBCorTot}(d-1) \tag{75}$$

The portion of this quantity, which is assigned to the interval is proportional to the interval's share of Enhanced Meal Insulin from the day before. This concept is applied in the following equation:

$$\text{deMealIns}(d,i) = \text{KrxInsl}*(1-\text{BoTFbk}(d-1))*\text{TBCorTot}(d-1)*\text{eMealIns}(d-1,i)/\text{eMealInsTot}(d-1) \tag{76}$$

$$\text{eMealIns}(d,i) = \text{eMealIns}(d-1,i) + \text{KrxInsl}*(1-\text{BoTFbk}(d-1))*\text{TBCorTot}(d-1)*\text{eMealIns}(d-1,i)/\text{eMealInsTot}(d-1) \tag{77}$$

Using equation (22) gives:

$$\text{CIR}(d,i) = \text{CarbSh}(d-1,i)/[\text{eMealIns}(d-1,i) + \text{KrxInsl}*(1-\text{BoTFbk}(d-1))*\text{TBCorTot}(d-1)*\text{eMealIns}(d-1,i)/\text{eMealInsTot}(d-1)] \tag{78}$$

As in the definition of a Basal Float, statement (60):

$$\text{BR}(d,i) = \text{BR}(d-1,i) + (\text{deRxInsl}(d,i) - \text{deMealIns}(d,i))/\text{dt}(i) \tag{79}$$

Using equation (70) gives:

$$\text{BR}(d,i) = \text{BR}(d-1,i) + \text{KrxInsl}*[\text{TBCorIns}(d-1,i+1) - (1-\text{BoTFbk}(d-1))*\text{TBCorTot}(d-1)*\text{eMealIns}(d-1,i)/\text{eMealInsTot}(d-1)]/\text{dt}(i) \tag{80}$$

This algorithm can be used in all time intervals "across the board". If used in all intervals, this algorithm has the effect of maintaining the original prescribed "shape" of the CIR or MealIns schedule; that is, each eMealIns(d,i) is multiplied by the same factor, so that they rise or fall in unison.

5.1.2.2 Basal Float 2, (deMealIns Value from Outside the Interval)

This algorithm is used in intervals where the MealIns or CIR value is borrowed from outside the interval (pegged to another interval.) This method is useful in non-meal time intervals, because meal insulin data in these intervals is not dependable enough for calculations. All the CIR's go up or down in proportion to the "Key CIR". The CIR schedule maintains the same "shape" and each CIR preserves the same ratio to the key CIR that it had on the first day, d=1. The key CIR may be chosen from several sources, usually from a time interval that has meals and uses a Meal Float algorithm. The number of the key CIR interval is keyc. The Enhanced insulin nomenclature system is used.

$$\text{CIR}(d,i) = [\text{CIR}(d-1,\text{keyc})/\text{CIR}(1,\text{keyc})]*\text{CIR}(1,i) \tag{81}$$

Equation (37) is adapted as shown below. The Enhanced nomenclature system is used, but note that the desired change is the same in both systems:

$$\text{deMealIns}(d,i) = \text{dMealIns}(d,i) = \text{CarbSh}(d-1,i)*[1/\text{CIR}(d,i) - 1/\text{CIR}(d-1,i)] \tag{82}$$

$$\text{BR}(d,i) = \text{BR}(d-1,i) + \text{dBR}(d,i) \tag{83}$$

The "Float" equation can be obtained from statement (60) as follows:

$$\text{BR}(d,i) = \text{BR}(d-1,i) + (\text{deRxInsl}(d,i) - \text{deMealIns}(d,i))/\text{dt}(i) \tag{84}$$

Then equation (56) is applied as follows:

$$\text{BR}(d,i) = \text{BR}(d-1,i) + [\text{KrxInsl}*\text{TBCorIns}(d-1,i+1) - \text{deMealIns}(d,i)]/\text{dt}(i) \tag{85}$$

$$\text{BR}(d,i) = \text{BR}(d-1,i) + [\text{KrxInsl}*\text{TBCorIns}(d-1,i+1) - \text{CarbSh}(d-1,i)*[1/\text{CIR}(d,i) - 1/\text{CIR}(d-1,i)]]/\text{dt}(i) \tag{86}$$

5.1.2.3 Meal Insulin Float 1

This algorithm pegs BR to a "Key" basal rate, i.e. all the basal rates go up or down in proportion to the key basal rate. The Basal schedule maintains the same "shape" and each Basal Rate preserves the same ratio to the key basal rate that it had on the first day, d=1. The key basal rate may be chosen from several sources, usually from a time interval that has no meals and uses a Basal Float algorithm. The key interval number is keyb. The Enhanced insulin nomenclature system is used.

$$\text{BR}(d,i) = [\text{BR}(d-1,\text{keyb})/\text{BR}(1,\text{keyb})]*\text{BR}(1,i) \tag{87}$$

The key basal rate can also be obtained from a calculation that uses the overall result of a Basal Float 1 algorithm, i.e. Basal(d-1) plus the correction. The formula uses d=1 like the one above.

$$\text{BR}(d,i) = [\text{Basal}(d-1) + \text{BoTFbk}(d-1)*\text{KrxInsl}*\text{TBCorTot}(d-1)]/\text{Basal}(1)*\text{BR}(1,i) \tag{88}$$

The key basal rate may also be obtained from:
From a sum of basal rates over all the intervals.

$$\text{Basal}(d) = \text{SUM}(\text{BR}(d,i)*\text{dt}(i)) \tag{89}$$

$$\text{BR}(d,i) = [(\text{Basal}(d)/\text{Basal}(1)]*\text{BR}(1,i) \tag{90}$$

Whatever the source of BR(d,i), the change in Basal Rate is:

$$\text{dBR}(d,i) = \text{BR}(d,i) - \text{BR}(d-1,i) \tag{91}$$

As in the definition of a Meal Insulin Float, statement (59):

$$\text{deMealIns}(d,i) = \text{KrxInsl}*\text{TBCorIns}(d-1,i+1) - \text{dBR}(d,i)*\text{dt}(i) \tag{92}$$

$$\text{deMealIns}(d,i) = \text{KrxInsl}*\text{TBCorIns}(d-1,i+1) - (\text{BR}(d,i) - \text{BR}(d-1,i))*\text{dt}(i) \tag{93}$$

$$\text{eMealIns}(d,i) = \text{eMealIns}(d-1,i) + \text{KrxInsl}*\text{TBCorIns}(d-1,i+1) - (\text{BR}(d,i) - \text{BR}(d-1,i))*\text{dt}(i) \tag{94}$$

Paraphrasing equation (22) gives:

$$\text{CIR}(d,i) = \text{CarbSh}(d-1,i)/\text{eMealIns}(d,i) \tag{95}$$

$$\text{CIR}(d,i) = \text{CarbSh}(d-1,i)/[\text{eMealIns}(d-1,i) + \text{KrxInsl}*\text{TBCorIns}(d-1,i+1) - (\text{BR}(d,i) - \text{BR}(d-1,i))*\text{dt}(i)] \tag{96}$$

5.1.2.4 Overview of 5.1.1.2 and 5.1.1.3

The Basal Float 2 algorithm is used in conjunction with the Meal Insulin 1 float as follows:

The practitioner's latest prescription is input for the first day, d=1. This data is the starting point for the automatic daily update sequence. The non-meal intervals are provided with Basal Float 2 algorithms, pegging their CIR's to a "Keyc" interval. One of the non-meal-containing intervals is nominated as the "Keyb" Basal Rate (usually the Late-Sleep interval or the average Basal/24). The Basal rates in the meal-containing intervals are pegged to the Key Basal Rate to maintain their original ratios to the key basal rate. The meal-containing intervals are provided with Meal Insulin Float algorithms.

5.1.2.5 Meal Float 2 (uses AMCorIns(i) as Error)

This algorithm makes use of after-meal BG testing. These tests and associated After-Meal Corrective Boluses divide the interval into two parts. The algorithm uses AMCorIns (d−1,i) as an "error" indicator for the first part of the interval, where the float is calculated. The value of dBasal(d−1,i) is obtained from the carb-free second part of the interval, which uses TBCorIns(d−1,i+1) as an error term for dBasal (d−1,i) The "Enhanced" insulin terminology is not used.

Define: Timeb(d−1,i)=The time of the after-meal bolus after the ith time boundary.

$$dtb(d-1,i)=\text{Time}(i+1)-\text{Timeb}(d-1,i) \quad (97)$$

$$dta(d-1,i)=\text{Timeb}(d-1,i)-\text{Time}(i) \quad (98)$$

In the second part of the interval:

$$BR(d,i)=BR(d-1,i)+\text{KrxInsl}*\text{TBCorIns}(d-1,i+1)/dtb(d-1,i) \quad (99)$$

Having obtained Basal Rate from the second part of the interval (or another source), the following statement can be said of the first part of the interval:

$$dBR(d,i)=BR(d,i)-BR(d-1,i) \quad (100)$$

$$\text{MealIns}(d,i)=\text{MealIns}(d-1,i)+\text{KrxInsl}*\text{AMCorIns}(d-1,i)-dBR(d,i)*dta(d-1,i) \quad (101)$$

$$CIR(d,i)=\text{CarbSh}(d-1,i)/\text{MealIns}(d,i) \quad (102)$$

5.1.3 For Multiple Dose Injection (MDI) and Inhaled Insulin.

The Basal insulin is administered in the form of long-acting insulin as infrequently as once per day. Corrective Insulin and Meal Insulin are administered as needed in the form of injected or inhaled short-acting insulin. This algorithm is suitable for "kits" in which the BG Meter and the insulin delivery device clip together or are otherwise linked, in order to maintain a combined digital history and a place for the program to reside.

5.1.3.1 Basal Float 1. (not used with MDI or Inhaled Insulin)
5.1.3.2 Basal Float 2, (The Value of dMealIns is from Outside the Interval)

This algorithm is used in intervals where the MealIns or CIR value is borrowed from outside the interval (pegged to another interval.) This method is useful in non-meal time intervals, because meal insulin data in these intervals is not dependable enough for calculations. All the CIR's rates go up or down in proportion to the "Key CIR". The CIR schedule maintains the same "shape" and each CIR preserves the same ratio to the key CIR that it had on the day of the most recent interaction with the Practitioner, d=1. The key CIR may be chosen from several sources, usually from a time interval that has meals and uses a Meal Float algorithm. The number of the key CIR interval is keyc. The Enhanced insulin nomenclature system is used.

$$CIR(d,i)=[CIR(d-1,\text{keyc})/CIR(1,\text{keyc})]*CIR(1,i) \quad (103)$$

Equation (37) is adapted as shown below. The Enhanced nomenclature system is used, but note that the desired change is the same in both systems:

$$\text{deMealIns}(d,i)=\text{dMealIns}(d,i)=\text{CarbSh}(d-1,i)*[1/CIR(d,i)-1/CIR(d-1,i)] \quad (104)$$

$$BR(d,i)=\text{Basal}(d-1)/24+dBR(i) \quad (105)$$

from equation (54) it can be seen that:

$$BR(d,i)=\text{Basal}(d-1)/24+(\text{deRxInsl}(d,i)-\text{deMealIns}(d,i))/dt(i) \quad (106)$$

$$BR(d,i)=\text{Basal}(d-1)/24+[\text{KrxInsl}*\text{TBCorIns}(d-1,i+1)-\text{deMealIns}(d,i)]/dt(i) \quad (107)$$

A non-meal interval using this algorithm (or some other suitable source) is used as the "reliable" data set. The resulting basal rate by equation (107) is used to determine the whole day's Basal.

$$\text{Basal}(d)=24*(\text{some conversion factor})*BR(d-1,\text{reliable}) \quad (108)$$

A recommended practice is the use of the Late-Sleep interval as the "reliable" interval. The following equation is given without explanation, as it will be covered by another section.

$$\text{Basal}(d)=24*Kf*BR(d-1,\text{LateSleep}) \quad (109)$$

5.1.3.3 Meal Insulin Float 1

The Enhanced insulin nomenclature system is used. This algorithm is used primarily for meal-containing intervals. The whole day's Basal(d) can be from a key interval's Basal Float calculation as in equation (109).

$$d\text{Basal}(d,i)=(\text{Basal}(d)-\text{Basal}(d-1))*dt(i)/24 \quad (110)$$

Whatever the source of Basal data, the Meal Insulin Float continues as follows:

The present invention calculates a schedule of new CIR (d,i) values, using the equation below, which is similar to equation (96):

$$CIR(d,i)=\text{CarbSh}(d-1,i)/[\text{eMealIns}(d-1,i)+\text{KrxInsl}*\text{TBCorIns}(d-1,i+1)-(\text{Basal}(d)-\text{Basal}(d-1))*dt(i)/24] \quad (111)$$

5.1.3.4 Overview of 6.1.3

The day's schedule is programmed as follows: An interval (usually a non-meal interval) is nominated as the "reliable" interval and is provided with a Basal Float 2 algorithm, with its CIR pegged to a meal interval. The BR from this "reliable" interval is used to determine the round-the-clock BR and the total daily Basal dose, which equals a constant (e.g. Kf or a constant of that type) times BRreliable times 24. The meal-containing intervals are provided with Meal Insulin Float algorithms and use the same single-valued round-the-clock BR. The non-meal intervals other than the "reliable" interval contain no calculations; their CIR's are pegged to a meal interval and their BR's are the same as all the others.

5.1.3.5 Meal Insulin Float 2, (uses AMCorIns(i) as an Error Term)

This algorithm makes use of after-meal BG testing. These tests and associated bolus divide the interval into two parts. The algorithm uses AMCorIns(d−1,i) as an "error" indicator for the first part of the interval, where the float is done.

Define: Timeb(d−1,i)=The time of the after-meal bolus after the ith time boundary.

$$dtb(d-1,i)=\text{Time}(i+1)-\text{Timeb}(d-1,i) \quad (112)$$

$$dta(d-1,i)=\text{Timeb}(d-1,i)-\text{Time}(i) \quad (113)$$

The Basal Rates are the same in all intervals; only Basal(d) is needed. It may be obtained from one of several sources.

The carb-free second part of the interval uses TBCorIns (d−1,i+1) as an error term for dBasal(d,i) The "Enhanced"

insulin terminology is not used. In the second part of the interval:

$$BR(d,i)=BR(d-1,i)+KrxInsl*TBCorIns(d-1,i+1)/dtb(d-1,i) \quad (114)$$

This result, obtained from a single "key" interval yields Basal(d):

$$Basal(d)=[BR(d,key)/BR(1,key)]*Basal(1) \quad (115)$$

The full schedule of results from the second part of the interval, equation (115) may be converted to a full day's basal as follows:

$$Basal(d)=SUM \text{ over } i[BR(d,i)*dt(i)] \quad (116)$$

A Basal Float 1 algorithm like version 6.1.2.1 in a "reliable" interval may be used to provide a round-the-clock basal rate.

A Basal Float 1 algorithm used in an overall manner, to obtain the day's total basal:

$$Basal(d)=[Basal(d-1)+BoTFbk(d-1)*KrxInsl*TBCorTot(d-1)] \quad (117)$$

Whatever the source for Basal(d), the following statement can be said of the first part of the interval:

$$MealIns(d,i)=MealIns(d-1,i)+KrxInsl*AMCorIns(d-1,i)-(Basal(d)-Basal(d-1)*dta(i)/24 \quad (118)$$

If the source is the second part of the interval, then this becomes:

$$MealIns(d,i)=MealIns(d-1,i)+KrxInsl*AMCorIns(d-1,i)-BoTFbk(d-1)*KrxInsl*TBCorTot(d-1)*dta(i)/24 \quad (119)$$

$$CIR(d,i)=CarbSh(d-1,i)/MealIns(d,i) \quad (120)$$

5.1.4 Skipped BG'S

Versions 1 and all sub-versions keep track of a special "virtual interval" consisting of the combined Early-Sleep and Late-Sleep intervals. This is for use in the event that the patient skips the Mid-Sleep BG test. A Basal Float calculation is kept current over this combined interval and is used to provide the basal rate for both component invervals if the BG test between them is skipped. This technique is used for often-skipped BG's like the Mid-Sleep BG just described. This technique can be used for any number of adjacent time intervals with skipped BG's on the boundaries. However, for seldom-skipped BG's it is more expedient to merely substitute BG=Target so that a zero value is calculated for CorIns(i). This causes no change and allows the previous value to remain. For this reason, the BG(d,i) parameters have default values of TargetAM or TargetTB until input is made.

5.1.5 A Modified Bolus Calculator

Many pump models provide a bolus calculator programmed inside. It performs the calculations in equations (20) and (14). The present invention treats exercise as a special adaptation of the Bolus calculator. There are input boxes for exercise in units of carbs, defining a new variable, ExerCarbs. The arithmetic difference between them is used as a variable Carbm shown below:

$$Carbm=Carbs-ExerCarbs \quad (121)$$

This may also be used for exercise alone without carbs. The modified Bolus Calculator also can calculate Correction Boluses. They must be designated "Time-Boundary" or "After-Meal" by the patient to flag the memory record and to select the correct one of the two targets: TargetAM and TargetTB. The modified boluses (meal and correction) are summed. If the result is positive, the pump infuses the calculated insulin amount as an ordinary bolus. If the result is negative, the pump suspends the Basal pumping for an amount of time calculated as follows:

$$TimeOut=-NegativeBolus(t)/BR(d,i) \quad (122)$$

Or it may reduce the basal for a time:

$$TimeReduced=-NegativeBolus(t)/(BR(d,i)-BRreduced) \quad (123)$$

5.1.6 Changing the Patient's Schedule

Section 1.1 above has described a normal 9 to 5 day. However, patients have many different schedules. To allow for this, the interval type is identified for each time interval by a parameter IntrvlType, which can have the following values:

M for "Meal Interval"

Kb for "keyb interval", typically the Late-Sleep interval, or other Non-Meal Interval in which food is never consumed.

Kc for "keyc interval" the source of pegged CIR's

S for "snack interval" in which food is occasionally consumed.

R for "reliable"

The adjustments to this feature are made by the Practitioner (not the patient unless it is with Practitioner guidance). The practitioner makes sure there is always a value of IntrvlType for each time interval. He or she can change this if desired. There is no restriction on the others. The present invention processes this data as follows:

---

If IntrvlType=Kb, go to Algorithm 6.1.2.3, Basal Float 2
   This results in a calculation of BR(d,keyb).
If IntrvlType=Kc, go to Algorithm 6.1.2.4, Meal Insulin Float 4
   This results in a calculation of BR(d,keyb).
If IntrvlType=R, go to Algorithm 6.1.2.3, Basal Float 2
   This results in a calculation of BRsimilar.
If IntrvlType = S go to Algorithm 6.1.2.3, Basal Float 2
If IntrvlType = M THEN:
   IF a Time-Boundary BG is missing, go to Algorithm 6.1.4
   IF an After-Meal Corrective Dose is present, go to Algorithm 6.1.2.6 Meal, Insulin Float 2
   ELSE go to Algorithm 6.1.2.4, Meal Insulin Float 1

---

5.2 Versions using Multiple-Days' Data:

Instead of re-adjusting the patient's parameters with the previous day's data, these Versions use the average accumulated data over the calendar period prior to the patient/practitioner interaction. The data for each time interval during the day is averaged separately over all the days. The day index, "d", is dropped and instead, the new parameters are distinguished from the current parameters as follows: Current parameters have no suffix. Calculated and recommended parameters have a suffix "rec". Prescribed parameters have suffix "rx". The "rx" parameters are input by the practitioner after considering the recommendations of the "rec" parameters. Parameters marked "Parameter(i)" are for the "ith" interval. Parameters with nothing in parentheses are non-scheduled parameters for which there is only one value for each patient/practitioner interaction. Thus "BRrec(i)" refers to the Recommended Basal Rate for the "ith" interval e.g. BRrec1, BRrec2 . . . etc, and BRrx(i) refers to the Prescribed Basal Rates.

5.2.1 Multiple Days' Data (Digital Advisor) for Practitioners $$KrxInsl \text{ is replaced by } deRxInsl/TBCorTot \text{ so} \quad (124)$$

$$deRxInsl(i)=deRxInsl/TBCorTot*TBCorIns(i+1) \quad (125)$$

Interactive Input Forms:

An exemplary form of the present invention is a two-table Access Database. There is a "one-to-many" relationship between the "patients' table", Tp and the "interactions table", Ti. There is a digital interactive Input Form (described in more detail in section 6.2.1.1.1.

The practitioner obtains some of the patients data by the exam or interview process. Other data is obtained by downloading the data from the pump and BG meter, either directly into the invention or by using the manufacturer's software to make printed copies, which are then transcribed into the invention's interactive digital input form manually. The manufacturer's downloading software normally provides a schedule of Bins (time periods enveloping the primary Time Boundaries) and calculates averages pertaining to each time boundary for several parameters including BG(i), AMCorIns (i), TBCorIns(i) and MealIns(i). (Recall as an example, that MealIns(i) represents the average of total Meal Insulin boluses within the ith Bin.)

5.2.1.1 For Pumps 5.2.1.1.1 Pump Type D and E

The formulas for pumps Types D and E are the simplest, so they will be discussed first.

Interactive Input Forms:

The main Input Form is the outer panel in FIG. 1. It collects the patient's permanent demographic data for table Tp. A SubForm (inner panel) collects the data from the patient/practitioner interaction for table Ti. The Sub Form has two pages that can be reached by the scroll bar. The first page (FIG. 1) addresses un-indexed parameters which have a single value for each patient/practitioner interaction. The second page (FIG. 2) addresses the standard modal day's schedule, containing the parameters with time-interval indexes like those referred-to herein in the manner of "parameter(i)"

5.2.1.1.1.1 Basal Float 1, (deMealIns is Proportional to eMealIns or Carbs)

This algorithm is similar to Basal Float algorithm 6.1.2.2 for Daily Update Version. The Enhanced insulin nomenclature system is used.

Transpose equation (52) to show that dBasal is determined by the other two parameters:

$$dBasal = deRxInsl - deMealIns \qquad (126)$$

$$dBasal(i) = deRxInsl(i) - deMealIns(i) \qquad (127)$$

deMealIns(i) is estimated by saying that the distribution of deMealIns among the intervals is proportional to the distribution of eMealIns, i.e.:

$$deMealIns(i) = deMealIns * eMealIns(i)/eMealInsTot \qquad (128)$$

$$eMealInsRec(i) = eMealIns(i) + deMealIns * eMealIns(i)/eMealInsTot \qquad (129)$$

By equation (22):

$$CIRrec(i) = CarbSh(i)/eMealInsRec(i) \qquad (130)$$

$$CIRrec(i) = CarbSh(i)/[eMealIns(i) + deMealIns * eMealIns(i)/eMealInsTot] \qquad (131)$$

Note that both eMealInsRec(i) and CIRrec(i) are merely the original value times an across-the-board factor. In the manner of statement (60), Basal is "Floated" by subtracting deMealIns(i) from deRxInsl(i):

$$BRrec(i) = BR(i) + [deRxInsl(i) - deMealIns(i)]/dt(i) \qquad (132)$$

Substituting equations (125) and (128) into this gives:

$$BRrec(i) = BR(i) + [deRxInsl/TBCorTot * TBCorIns(i+1) - deMealIns * eMealIns(i)/eMealInsTot]/dt(i) \qquad (133)$$

Also calculated is the value of:

$$BRaveRec = (Basal + deRxInsl - deMealIns)/24 \qquad (134)$$

The practitioner uses this version of the invention as follows:

When all the patient's data has been input from downloads or otherwise, The Basal Float is almost ready to calculate the main goals (a schedule of recommended basal rates, BRrec(i) and a schedule of recommended CIRrec(i)). The practitioner needs to input at least two of the three quantities in equation (126). The present invention will do the rest. So, the practitioner looks over the data obtained so far, particularly TBCorTot. Then he or she makes a judgment as to "How much of TBCorTot do I want to add to Prescription Insulin as a change?" Then he or she inputs deRxInsl, which must be within the built-in input limits (see section: Limited Domain). Basal(i) will be "floated", so the other quantity needed from the practitioner is deMealIns. Before inputting he must ask himself, "When I prescribe this change, deRxInsl, how much of it do I want to assign to Enhanced Meal Insulin?" He can make this judgement by comparing the ratio of Basal/TDDavg (known as BoT in the present embodiment) to the optimum value from the AIM statistical studies (48% from latest publication). For instance, if Basal is too high he can use greater than half of deRxInsl as deMealIns. This will raise deMealIns relative to deRxInsl, thus lowering Basal. There may be other considerations of a medical nature that may influence the practitioner's decision. The choice of deMealIns may have input limits. The outputs are BRrec(i), BRavgRec, and CIRrec(i) as calculated by the equations above. The practitioner considers these recommended values and inputs the "rx" values based upon his judgment.

5.2.1.1.1.2 Basal Float 2, (not used with Multiple Days' Data)

5.2.1.1.1.3 Meal Insulin Float 1

This Version is similar to the Version 6.1.2.4, Meal Insulin Float. For input, it requires the Prescribed Basal Rates, BRrx(i), which are input by the Practitioner. The Practitioner may desire "advice" before inputting BRrx(i). The values of BRrec(i) and BRaveRec from the result of Version 6.2.1.1.1.1, Basal Float 1, above, are good advice, so they are provided on the same computer screen Input Form. The value of BRf from the Kf calculator is also good advice. The Enhanced insulin nomenclature system is used.

Transpose equations (52) and (54) to show that deMealIns is determined by the other two parameters:

$$deMealIns = deRxInsl - dBasal \qquad (135)$$

$$deMealIns(i) = deRxInsl(i) - dBasal(i) \qquad (136)$$

$$BRrx(i) = \text{input by practitioner} \qquad (137)$$

The "Float" is very similar to equation (93); it is set up as follows:

Equation (124) is used to modify equation (93) with the result below:

$$deMealIns(i) = (deRxInsl/TBCorTot) * TBCorIns(i+1) - (BRrx(i) - BR(i)) * dt(i) \qquad (138)$$

$$eMealInsRec(i) = eMealIns(i) + deRxInsl/TBCorTot * TBCorIns(i+1) - (BRrx(i) - BR(i)) * dt(i) \qquad (139)$$

Using equation (22) gives:

$$\text{CIRrec}(i) = \text{CarbSh}(i)/\text{eMealInsRec}(i) \tag{140}$$

$$\text{CIRrec}(i) = \text{CarbSh}(i)/[\text{eMealIns}(i) + \text{deRxInsl}/\\ \text{TBCorTot} * \text{TBCorIns}(i+1) - (\text{BRrx}(i) - \text{BR}(i)) * \text{dt}\\ (i)] \tag{141}$$

The Practitioner considers this schedule of CIRrec(i) and then inputs:

$$\text{CIRrx}(i) = \text{input by the Practitioner} \tag{142}$$

5.2.1.1.1.4 Overview of 6.2.1.1.1.1 and 6.2.1.1.1.3 Multiple Days' Data, Pump Type D Recommendations are provided for Basal Float and Meal Insulin Float on the same Input Form (see FIG. 2), so that the practitioner can consider Basal Float recommendations, BRrec(i), BRaveRec, and BRf when filling in the prescribed BRrx(i) schedule. The Meal Insulin Float uses these "BRrx (i)" values as input. Then it calculates CIRrec(i) as output for the meal-containing intervals. Then the Practitioner fills in the blanks for CIRrx(i). Backtracking the discussion a little: The practitioner's choice of BRrx(i) is very influential. Discussion:

The practitioner can use all of the BRrec(i) values as BRrx(i) if desired. This has the effect of changing the entire meal insulin (or CIR) schedule by the same factor across the board.

or

A simple basal schedule can be used to give the patient more meal-skipping flexibility, as mentioned earlier. For instance:

The practitioner can use the BR's for non-meal intervals "as is". This probably will include the "Early-Sleep" and "Late-Sleep" intervals.

The Practitioner can use a single carefully-judged Fasting Basal Rate, BRf, to underlie the meal intervals. Determining this basal rate is one of the Practitioner's major tasks. The BRf Calculator may be used at the Practitioner's discretion.

5.2.1.1.1.5 Meal Insulin Float 2 (uses AMCorIns as the Error)

This algorithm makes use of after-meal BG testing. These tests divide the interval into two parts. The algorithm uses AMCorIns(i) as an "error" indicator for the first part of the interval, where the float is done. The value of dBasal(i) is obtained from the carb-free second part of the interval, which uses TBCorIns(i+1) as an error term for dBasal(i). The "Enhanced" insulin terminology is NOT used.

Define: Timeb(i)=The time of the after-meal bolus after the ith time boundary.

$$\text{dta}(i) = \text{Timeb}(i) - \text{Time}(i) \tag{143}$$

$$\text{dtb}(i) = \text{Time}(i+1) - \text{Timeb}(i) \tag{144}$$

In the second part of the interval:

$$\text{BRrec}(i) = \text{BR}(i) + \text{KrxInsl} * \text{TBCorIns}(i+1)/\text{dtb}(i) \tag{145}$$

$$\text{dBR}(I) = \text{BRrec}(i) - \text{BR}(i) \tag{146}$$

Having obtained Basal Rate from the second part of the interval (or other source), the following statement can be said of the first part of the interval:

$$\text{MealInsRec}(i) = \text{MealIns}(i) + \text{KrxInsl} * \text{AMCorIns}(i) -\\ \text{dBR}(i) * \text{dta}(i) \tag{147}$$

If the second part of the interval was used, this becomes:

$$\text{MealInsRec}(i) = \text{MealIns}(i) + \text{KrxInsl} * \text{AMCorIns}(i) - \text{dta}\\ (i) * \text{KrxInsl} * \text{TBCorIns}(i+1)/\text{dtb}(i) \tag{148}$$

$$\text{CIRrec}(i) = \text{CarbSh}(i)/\text{MealInsRec}(d,i) \tag{149}$$

If desired, the factor KrxInsl may be obtained from dRxInsl input by the practitioner as described earlier:

$$\text{KrxInsl} = \text{dRxInsl}/(\text{AMCorTot} + \text{TBCorTot}) \tag{150}$$

Alternatively, KrxInsl may be replaced by two "K-factors", one for each part of the time interval: KrxInsAM and KrxInsTB:

First, Basal Rate is determined from the second part of the interval:

$$\text{BRrec}(i) = \text{BR}(i) + \text{KrxInsTB} * \text{TBCorIns}(i+1)/\text{dtb}(i) \tag{151}$$

Then Meal Insulin is determined from the first part of the interval:

$$\text{MealInsRec}(i) = \text{MealIns}(i) + \text{KrxInsAM} * \text{AMCorIns}(i) -\\ \text{dta}(i) * \text{KrxInsTB} * \text{TBCorIns}(i+1)/\text{dtb}(I) \tag{152}$$

$$\text{CIRrec}(i) = \text{CarbSh}(i)/\text{MealInsRec}(d,i) \tag{153}$$

This alternative method may shift the Basal/TDD ratio and may be useful if such a result is intended.

5.2.1.1.2 Pump Type C

Pumps of these types are intermediate between Types A and D. The algorithms of 6.2.1.1.1.1 and 6.2.1.1.1.3 and their overview are applicable to Type B pumps, except that:

TBCorIns(i) is not available, so it must be calculated by the formula:

$$\text{TBCorIns}(i) = \text{AVG over calendar period of }((\text{BG}(t) -\\ \text{TargetTB})/\text{CF}) \tag{154}$$

AMCorIns(i) is not available so Meal Float 2 cannot be used.

5.2.1.1.3 Pump Type B

Pumps of these types are intermediate between Types A and C. The algorithms of 6.2.1.1.1.1, 6.2.1.1.1.3, and their Overview are applicable to Type B pumps, except that in addition to the limitations of Pump Type C:

MealIns(i) is not available, so dMealIns(i) is estimated by:

$$\text{dMealIns}(i) = \text{dMealIns} * \text{CarbSh}(i)/\text{CarbShTot} \tag{155}$$

5.2.1.1.4 Pump Type A

Type A pumps are the simplest, but have complicated formulas for the reason that the values for the absent parameters must be calculated using estimation formulas. These estimation formulas add complexity. In addition to the limitations of Type B pumps, the Type A pumps are limited as follows:

Because of the lack of data, the only appropriate algorithm for Type A pumps is "Basal Float 1, similar to Version 6.2.1.1.1.1.

There are no memories for BG(i), so values for TBCorIns (i) and AMCorIns(i) must be calculated from BG data downloaded from the BG meter. This data may contain anomalous or unused BG test results and is not as dependable as the BG data from the pump's memory.

There are no memories for CarbSh(i), so the practitioner must estimate. The only use of the data is in the ratio CarbSh(i)/CarbShTot, so the units do not matter; the practitioner may use grams, exchanges, percent of total, units of insulin, or any other units proportional to Meal Insulin.

The lack of good data makes CIR hard to calculate. A single CIR is calculated for use round-the-clock. The differential formula (34) is used:

$$\text{dCIRcalcA} = [-(\text{Kcir} * \text{Wt} * 2/\text{TDDavg}^2] * \text{deMealIns} \tag{156}$$

A slight complication is that Type A pumps have no memory for CIR, so the patient must keep track of it. To make this easier for the patient, only integer (or half integer values for CIR<8) are prescribed. Therefore, a two-step manual input is used:

dCIRcalcA is calculated by the invention and appears on the screen. The practitioner rounds it to the preferred rounded quantity and puts the value back into the reverse equation as dCIR. Then the invention calculates:

$$deMealInsCalcA=-dCIR/(Kcir*Wt*2/TDDavg^2) \quad (157)$$

Then the practitioner inputs this value into the box for deMealIns. Not surprisingly, the resulting value of dCIR-calcA is integer-valued. The recommended value, CIRrecA, is automatically calculated as follows:

$$CIRrecA=dCIRcalcA+CIR \quad (158)$$

5.2.1.2 Subcutaneous Multiple Dose and Inhaled Insulin

Manual injection patients usually use two types of insulin:
Long-acting insulin for "basal" injections as infrequently as once per day
Short-acting insulin for meal and correction boluses.
The insulin delivery devices include "pens" and inhalers.
There are "kits' currently being developed that consist of a BG meter that clips or links to an insulin-delivery device (an insulin injection "pen" or an insulin inhaler) in such a way that the data is shared. The BG test results are used to calculate a corrective insulin dose automatically, and the insulin delivery device is automatically set for use. Also, carbs can be entered manually so that Meal Insulin Boluses are similarly calculated and pre-set. Digital memory is available in either the meter or the insulin delivery device so that the combined BG and insulin history can be downloaded by the Practitioner.

There are several types of insulin available. The input form contains input boxes for the brand names or generic names of the two types of insulin prescribed.

The formulas deal with basal amounts in each time interval, rather than basal rates. The long time-response of the long-acting insulin makes Basal Rate schedule adjustments impractical.

5.2.1.2.1 Basal Float 1

The partnership of Basal Float 1 and Meal Insulin Float 1 may be employed in a similar manner to pumps Types D and E. Similarities and differences: As in pumps the Practitioner inputs deRxInsl and deMealIns. The input boxes for BR(i) are replaced by a single box for Basal, a single BR is calculated (one twenty-fourth of Basal). The values of BRrec(i) are shown individually as in pumps. As in pumps, a value is calculated for BRaveRec using equation (141). All the BRrx(i) are replaced by a single box for BRrx, and Basalrx is calculated (24 times BRrx). After reviewing the recommendations for Basal and Basal Rate, the Practitioner inputs BRrx

5.2.1.2.2 Meal Insulin Float 1

The Meal Insulin Float 1 is similar to that used with Type D pumps. The Enhanced insulin nomenclature system is used.

The value of BasalRx from the previous section (or some other source) is used as input by the Meal Insulin Float 1 algorithm.

$$dBasal(i)=(Basalrx-Basal)*dt(i)/24 \quad (159)$$

The present invention then calculates a schedule of recommended CIRrec(i) values, using a Meal Insulin Float. The formula is adapted from equation (96) by applying equation (124):

$$CIRrec(i)=CarbSh(i)/[eMealIns(i)+ \\ (deRxInsl*TBCorIns(i+1)/TBCorTot-(BaslRx- \\ Basal)*dt(i)/24] \quad (160)$$

5.2.1.2.3 Meal Insulin Float 2 (uses AMCorIns(i) as an Error)

This algorithm makes use of after-meal BG testing. These tests and associated boluses divide the interval into two parts.

Define: Timeb(i)=The time of the after-meal bolus after the ith time boundary.

$$dtb(i)=Time(i+1)-Timeb(i) \quad (161)$$

$$dta(i)=Timeb(i)-Time(i) \quad (162)$$

The algorithm uses AMCorIns(i) as an "error" indicator for the first part of the interval, where the float is calculated. A figure for BasalRx is needed. The Practitioner places it in an input box after reviewing the invention's calculated recommendations, which may be one or more of the following:

BasalRec may be obtained from the carb-free second part of the interval, which uses TBCorIns(i+1) as an error term for dBasal(i) The "Enhanced" insulin terminology is not used. In the second part of the interval:

$$BRrec(i)=BR(i)+KrxInsl*TBCorIns(i+1)/dtb(i) \quad (163)$$

or

This result from a "reliable" interval may be converted to a full day's basal as follows:

$$BasalRec=BRreliable*Kf*24 \quad (164)$$

or

BasalRec may be obtained from the sum of the results above:

$$BasalRec=SUM \text{ over } i(BRrec(i)*dt(i)) \quad (165)$$

or

BasalRec may be obtained from a Basal Float 1 calculation in a "reliable" interval. This result is converted in the same manner as equation (164)

or

Another source of BasalRec is the total recommended Basal from a Basal Float 1 algorithm, converted in the same manner as equation (165)

Whatever the source for BasalRec, the Practitioner inputs BasalRx. The following statement can be said of the first part of the interval:

$$MealInsRec(i)=MealIns(i)+KrxInsl*AMCorIns(i)- \\ Basal*dta(i)/24 \quad (166)$$

$$CIRrec(i)=CarbSh(i)/MealInsRec(i) \quad (167)$$

The factor KrxInsl may be obtained from dRxInsl input by the practitioner as described earlier:

$$KrxInsl=dRxInsl/(AMCorTot+TBCorTot) \quad (168)$$

Alternatively, if the method of equation (163) is used, KrxInsl may be replaced by two "K-factors", one for each part of the time interval: KrxInsAM and KrxInsTB:

First, Basal Rate is determined from the second part of the interval:

$$BRrec(i)=BR(i)+KrxInsTB*TBCorIns(i+1)/dtb(i) \quad (169)$$

Then Meal Insulin is determined from the first part of the interval:

$$MealInsRec(i)=MealIns(i)+KrxInsAM*AMCorIns(i)- \\ dta(i)*KrxInsTB*TBCorIns(i+1)/dtb(i) \quad (170)$$

$$CIRrec(i)=CarbSh(i)/MealInsRec(d,i) \quad (171)$$

This alternative method may shift the Basal/TDD ratio and may be useful if such a result is intended.

5.2.1.3 Limited Domain of deRxInsl and the Safety-Net Formula for Multiple Days' Data Versions

5.2.1.3.1 Limited Domain of deRxInsl

The Float formulas using Multiple Days' Data for whole intervals work only within certain limits in which the changes called for are less than TBCorTot and in the same direction (same sign).

Both these conditions are contained in the requirement that $$\text{TBCorTot/deRxInsl} > 1 \tag{172}$$

If the parameters go beyond this limit then nonsensical results occur. To prevent this from happening and to provide a further margin of safety, there are input limits placed upon the parameters to prevent the Practitioner from inputting numbers out of the acceptable range. The input limit is in the form of the parameter KrxInslMax. The limit is in the form:

$$\text{TBCorTot/deRxInsl} \geq 1/\text{KrxInslMax} \tag{173}$$

If KrxInslMax≤1, then the nonsensical results are avoided. The value of 0.5 is currently in use.

5.2.1.3.2 Safety-Net Formula:

5.2.1.3.2.1 For Basal Float 1

As mentioned above, the Float formulas using Multiple Days' Data work only within certain limits. The first line of defense is the input limits mentioned above. However, there may be ways to circumvent the input limits, on purpose or accidentally. To protect against this possibility, there is a second line of defense, the safety net formulas. Each of the Float formulas actually uses two formulas for deRxInsl(i), each over a different domain of deRxInsl.

Small Domain: This is the "acceptable" domain, using the formulas discussed so far. If TBCorTot/deRxInsl>1, then the formula below is used. It produces accurate results over its limited domain in which the changes called for are less than or equal to the Total Enhanced Corrective Insulin and in the same direction. It apportions to each time interval a small amount of the deRxInsl proportional to the time interval's share of the TBCorTot. Most patient/practitioner interactions are in the small domain. The "small domain" formula has been discussed earlier. It is re-written below. The suffix "sd" is added to the name the name to show what it is:

$$\text{deRxInslsd}(i) = \text{deRxInsl} \cdot \text{TBCorIns}(i+1)/\text{TBCorTot} \tag{174}$$

Large Domain: The formula introduced below is a backup to the input limits placed upon deRxInsl. If the desired change to deRxInsl is not in the small domain, i.e. if TBCorTot/deRxInsl<1, then the formula below is used. It produces a less accurate but safe result when the changes called for are larger than TBCorTot or in the direction opposite to TBCorTot. The right-hand side starts with the full corrective insulin for the time interval. Then the "overshoot" of deRxInsl over TBCorTot is apportioned among the time intervals, but the apportioning fraction includes Basal as well as Enhanced Corrective Insulin, making it a less sensitive fraction, but less exact. In its role as a backup to the input limits, the large domain formulas are designed never to be used. The Safety-Net formula for Type D pumps, Basal Float 1 Algorithm 6.2.1.1.1.1, is as follows:

$$\text{deRxInslld}(i) = \text{TBCorIns}(i+1) + (\text{deRxInsl} - \text{TBCorTot}) \cdot (\text{TBCorIns}(i+1) + \text{Basal}(i))/(\text{TBCorTot} + \text{Basal}) \tag{175}$$

The transition between these two formulas is accomplished by a logical variable called Swtch, which has a value of zero (0) in the small domain and one (1) in the large domain.

$$\text{IF(TBCorTot/deRxInsl} \geq 1) \text{ THEN Swtch}=0 \text{ ELSE Swtch}=1 \tag{176}$$

The invention accomplishes this as follows:

$$\text{Swtch}=\text{IF(TBCorTot/deRxInsl} \geq 1,0,1) \tag{177}$$

Swtch helps to put the two equations together into a single equation, which is switched from (174) to (175) as needed. This is shown below:

$$\text{deRxInsl}(i)=\text{swtch} \cdot \text{deRxInslld}(i)+(1-\text{swtch}) \cdot \text{deRxInslsd}(i) \tag{178}$$

After substituting the large and small domain formulas into this, it reduces to the following equation, which requires fewer computer fields:

$$\text{deRxInsl}(i)=\text{swtch} \cdot \text{TBCorIns}(i+1)+(\text{deRxInsl}-\text{Swtch} \cdot \text{TBCorTot}) \cdot (\text{TBCorIns}(i+1)+\text{Swtch} \cdot \text{Basal}(i))/(\text{TBCorTot}+\text{Swtch} \cdot \text{Basal}) \tag{179}$$

This equation in turn is substituted into one of the Float equations, e.g. equation (133) to yield the result below, which produces a schedule of recommended basal rates.

$$\text{BRrec}(i)=[\text{Basal}(i)+\text{Swtch} \cdot \text{TBCorIns}(i+1)+(\text{deRxInsl}-\text{Swtch} \cdot \text{TBCorTot}) \cdot (\text{TBCorIns}(i+1)+\text{Swtch} \cdot \text{Basal}(i))/(\text{TBCorTot}+\text{Swtch} \cdot \text{Basal})-\text{dMealIns} \cdot \text{CarbSh}(i)/\text{CarbShTot}]/\text{dt}(i) \tag{180}$$

For Pump Types A, TBCorInsA(i) is substituted for TBCorIns(i) and TBCorTotA for TBCorTot in the above equation.

5.2.1.3.2.2 For Meal Insulin Float 1

The same definitions of the two domains for deRxInsl are used in the Meal Insulin Float formulas, Algorithm 6.2.1.1.1.3 Leading to:

$$\text{eMealInsRec}(i)=\text{eMealIns}(i)+\text{Swtch} \cdot \text{TBCorIns}(i+1)+(\text{deRxInsl}-\text{Swtch} \cdot \text{TBCorTot}) \cdot [\text{TBCorIns}(i+1)+\text{Swtch} \cdot \text{eMealIns}(i)]/[\text{TBCorTot}+\text{Swtch} \cdot \text{eMealInsTot}]-(\text{BRrx}(i)-\text{BR}(i)) \cdot \text{dt}(i) \tag{181}$$

This is converted to CIRrec(i) by an adaptation of equation (22):

$$\text{CIRrec}(i)=\text{CarbSh}(i)/\text{eMealInsRec}(i) \tag{182}$$

$$\text{CIRrec}(i)=\text{CarbSh}(i)/[\text{eMealIns}(i)+\text{swtch} \cdot \text{TBCorTot}+(\text{deRxInsl}-\text{swtch} \cdot \text{TBCorTot}) \cdot (\text{TBCorIns}(i+1)+\text{swtch} \cdot \text{eMealIns}(i))/(\text{TBCorTot}+\text{swtch} \cdot \text{eMealInsTot})-\text{dt}(i) \cdot (\text{BRrx}(i)-\text{BR}(i))] \tag{183}$$

Where Swtch is the same "switching parameter" introduced earlier by equation (182) to shift the formula between two different domains.

5.2.1.3.2.3 For Meal Insulin Float 2 (uses AMCorIns(i) as Error)

Small Domain:
Over the whole interval:

$$\text{dRxInslsd}(i)=[\text{dRxInsl}/(\text{AMCorTot}+\text{TBCorTot})] \cdot (\text{AMCorIns}(i)+\text{TBCorIns}(i)) \tag{184}$$

This can be thought of as an equation in two parts:
For the last part of the interval:

$$\text{dRxInslsdb}(i)=[\text{dRxInsl}/(\text{AMCorTot}+\text{TBCorTot})] \cdot \text{TBCorIns}(i)=\text{dBasalb}(i) \tag{185}$$

Note that this is all Basal Insulin.
For the first part of the interval:

$$\text{dRxInslsda}(i)=[\text{dRxInsl}/(\text{AMCorTot}+\text{TBCorTot})] \cdot \text{AMCorIns}(i) \tag{186}$$

Large Domain:
For the last part of the interval:

$$dRxInslldb(i)=TBCorTot(i)+(dRxInsl-AMCorTot-TBCorTot)*(TBCorIns(i)+BR(i)*dtb(i))/(AMCorTot+TBCorTot+Basal) \quad (187)$$

For the first part of the interval:

$$dRxInsllda(i)=AMCorIns(i)+(dRxInsl-AMCorTot-TBCorTot)*(AMCorIns(i)+BR(i)*dta(i))/(AMCorTot+TBCorTot+Basal) \quad (188)$$

The sum of the two corrective insulin totals must be used in the switch parameter.

$$Swtchm=IF((AMCorTot+TBCorTot)/dRxInsl>=1,0,1) \quad (189)$$

5.2.2 Automatic Multiple Days' Data (Digital Advisor)

The descriptions so far in Version 2 describe the "manual" version of the Multiple Past Days' algorithm. The automatic features described below are to remove the pauses for human judgement and input.

5.2.2.1 Automation of deRxInsl:

To automate the parameter deRxInsl, the present invention makes use of the fact that it is more difficult to control the diabetes of a patient whose BG tests, have a high percent standard deviation, (BGsd/BGmean) compared to the database norm. The present invention uses a simple ramp function for this as shown below:

Some new parameters:

FInsAuto is a multiplier for use in the formula for deRxInsAuto as follows:

$$deRxInsAuto=FInsAuto*KrxInslMax*TBCorTot \quad (190)$$

where

KrxInslMax is a positive constant <=1, introduced earlier. It is subject to change by the programmers if necessary. The present value is 0.5.

Two definitions:

PmPctBGsd: Database "population" mean of the quantity (BGsd/BGmean).

PsdPctBGsd: Database "population" standard deviation of the quantity (BGsd/BGmean), i.e. the database standard deviation of the personal standard deviations.

In the present invention, FInsAuto is a ramp function as follows:

```
IF BGsd/BGmean<PmPctBGsd+PsdPctBGsd then
   FInsAuto=1 IF PmPctBGsd+
   PsdPctBGsd<=BGsd/Bgmean<=PmPctBGsd+2
   PsdPctBGsd, THEN FInsAuto=[1-(BGsd/Bg-
   mean-PmPctBGsd-PsdPctBGsd)/PsdPctBGsd]
   IF BGsd/BGmean>PmPctBGsd+2 PsdPctBGsd
   then FInsAuto=0                                    (191)
```

This function describes a flat region followed by a ramp down to zero as shown in FIG. 3.

5.2.2.2 Automation of deMealIns:

The present invention makes use of the parameter dBslToTgt, which is a general advisory parameter that shows what change in Basal is necessary to achieve BoTTgt.

$$dBslToTgt=TDD*BoTTgt-Basal \quad (192)$$

Two steps are employed to automate dMealIns:

The first equation below assigns to the change an absolute value equal to the minimum absolute value of deRxInsl or dBaslToTgt. The reason is to avoid overshooting either BoTTgt or deRxInsl. The second equation uses the result from the first, together with equation (57), to calculate a max value for deMealInsAuto; then it limits deMealInsAuto to Kmauto times its max value if it is positive (in the direction of adding insulin). The parameter Kmauto is subject to adjustment by the programmers.

$$dBasalAuto=IF[ABS(dBaslToTgt/deRxInsl)<1,ABS(dBaslToTgt), ABS(deRxInsl)]*sgn(dBaslToTgt) \quad (193)$$

$$deMealInsAuto=IF[(deRxInsl>dBasalAuto,Kmauto*(deRxInsl-dBasalAuto),(deRxInsl-dBasalAuto)] \quad (194)$$

where Kmauto is a positive constant <=1, presently set at 1.

The value of BoTTgt may be obtained from the AIM study's value for Kb or from BoTTgtRec from Section 6.1.2.1 Basal-to-Total Ratio 5.2.2.3 Automatic Rounding of CIR for Pump Type A:

In the manual mode for Type A, a two-step process is required to obtain a half-integer value for CIR in the range below 8. The automatic feature accomplishes this by multiplying the floating point number dCIRcalcA by two, then rounding off to a whole number, and then dividing by two. The result is input into the reverse equation to correct the dMealIns for the change.

5.3 Non-Float Algorithm

This algorithm uses the BoTFbk(d) factor to determine both Basal Rate and CIR. This type of algorithm is shown below in a Daily Update Version:

$$eMealIns(d,i)=eMealIns(d-1,i)+KrxInsl*(1-BoTFbk(d-1))*TBCorIns(d-1,i+1) \quad (195)$$

$$CIR(d,i)=CIR(d-1,i)-KrxInsl*(1-BoTFbk(d-1))*eCorIns(d-1,i+1)*CIR(d-1,i)/eMealIns(d-1,i) \quad (196)$$

$$BR(d,i)=BR(d-1,i)+KrxInsl*BoTFbk(d-1)*TBCorIns(d-1,i+1) \quad (197)$$

This method has the advantage of being very accurate, but has the disadvantage of assigning large changes in meal insulin to time intervals that have little to no carb consumption. For this reason, the version is suitable only for the intervals containing the main meals.

6. Time Intervals

Theoretically, there should be no limit on the number of time intervals in the day. However, for reasons of screen space, there is a limit on the number of time intervals that may be used. Also, for an individual patient, fewer than the screen's maximum may be used. The invention needs to find the last one. The last time boundary of the day (before midnight) is called Tmax. It is found by a routine that picks out the time boundary with the highest 24-hour clock time. This routine is incorporated into a single formula of nested IF statements shown below. (note: In MS Access the NZ function makes nulls and zeros act the same):

```
Tmax=IIf([Time1])>NZ([Time2]),[Time1],IIf(NZ
   ([Time2])>NZ([Time3]),[Time2],IIf(NZ
   ([Time3])>NZ([Time4]),[Time3],IIf(NZ
   ([Time4])>NZ([Time5]),[Time4],IIf(NZ
   ([Time5])>NZ([Time6],[Time5],
   IIf(NZ([Time6])>NZ([Time7]),[Time6],
   [Time7])))))                                       (198)
```

The Time Intervals, dt(i), are found by subtracting the consecutive time boundaries.

$$dt(i)=time(i+1)-time(i) \quad \text{copy of (4)}$$

Special mention should be made of the interval surrounding midnight.

$$dt0=24+time1-Tmax \quad \text{copy of (5)}$$

6.1 Finding the Day's Last Entry

Since people rarely go to bed exactly at midnight, it often occurs that some parameters normally associated with bedtime affect the early morning time interval. For instance, Meal Insulin taken at bedtime affects the Corrective Insulin of the mid-sleep time boundary. The formula below will find the last entry of the day:

[MealInsLast]=IIF([Time2]=[Tmax],[MealIns2],0)+
    IIF([Time3]=[Tmax],[MealIns3],0)+
    IIF([Time4]=[Tmax],[MealIns4],0)+
    IIF([Time5]=[Tmax],[MealIns5],0)+
    IIF([Time6]=[Tmax],[MealIns6],0)+IIF([Time7]
    =[Tmax],[MealIns7],0)    (199)

The recommended values for the last time interval in the day need to be re-located on the screen. The following is an example using Recommended Basal Rate, BR:

BRrec(i)=IIF([Time(i)]=[Tmax],[BRrecLast],[BRrec
    (i) regular formula])    (200)

Other alternative embodiments will become apparent to those skilled in the art to which an exemplary embodiment pertains without departing from its scope and spirit.

REFERENCES

1. Paul C Davidson, Harry R Hebblewhite, Bruce W Bode, Pat L Richardson, R Dennis Steed, N Spencer Welch, and Joseph Johnson; "Statistical Estimates for CSII Parameters: Carbohydrate-to-Insulin Ratio (CIR, 2.8 Rule); Correction Factor (CF, 1700 Rule); and Basal Insulin"; Diabetes Technology Meeting Poster, Oct. 31, 2002. (Will be published in Diabetes Technology and Therapeutics April 2003.
2. John Walsh, Ruth Roberts, Varma Chandrasekhar, and Timothy Bailey; USING INSULIN, 2003

Addendum A

SQL listing for Multiple Day's Data Version for Insulin Pumps (Type C). This Version of the Invention is embodied in a Microsoft Access database for use by the Practitioner as he/she interacts with a patient.

```
* * * * * * * * * * * * * * * * * * * * * * * * * * * * * * * * * * * * *
SELECT TI.Tp_PatientID, TP.SSN, TP.Name, TP.Endo, TP.DOB, TP.Sex,
TP.OnsetDMdate, TP.PumpStartDate, TP.PhoneNos, TP.Email,
TI.IntractionID, TI.IntrDate,
TI.Hgt, TI.Wt, TI.HbA1c, TI.Creatinine, TI.Microalb,
TI.BGmean, TI.BGsd, TI.BGpd, TI.NBGs,
TI.TDDa, TI.TDDb, TI.TDDc, TI.TDDd, TI.TDDe, TI.TDDf,
(NZ([TDDa])+NZ([TDDb])+NZ([TDDc])+NZ([TDDd])+NZ([TDDe])+NZ([TDDf]))/(-
IsNumeric([TDDa])-IsNumeric([TDDb])-IsNumeric([TDDc])-IsNumeric([TDDd])-
IsNumeric([TDDe])-IsNumeric([TDDf])) AS TDDavg,
[Basal]/[TDDavg] AS BasalOvrTDD,
0.48*[TDDavg] AS BasalAIM,
[BasalAIM]-[Basal] AS dBslToAIM,
TI.Basalrx,
TI.TargetBG, TI.TargetBGrx,
TI.CF, 1708/[TDDavg] AS CFaim, TI.CFrx,
TI.CIR, 2.81*[wt]/[TDDavg] AS CIRaim,
IIf([sex]="m",(([Hgt]-60)*6+106)*13/8,(([Hgt]-60)*5+100)*13/8) AS [Carbspd(Hgt)],
1-[CarbShTot]*0.8/[Carbspd(Hgt)] AS BoTTgtRec,
[CarbShTot]/[eMealInsTot] AS [CIR(carb)], TI.MealInsTotARx,
[CarbShTot]/[MealInsTotARx] AS [CIR(MealIns1Rx)],
TI.TypeInsShort, TI.TypeInsLong,
TI.Diet, TI.PumpType, TI.iComment,
TI.TimeLabl2, TI.TimeLabl3, TI.TimeLabl4, TI.TimeLabl5, TI.TimeLabl6,
TI.TimeLabl7, TI.TimeLabl8,
0 AS Time1, TI.Time2, TI.Time3, TI.Time4, TI.Time5, TI.Time6, TI.Time7, TI.Time8,
IIf(NZ([Time2])>NZ([Time3]),[Time2],IIf(NZ([Time3])>NZ([Time4]),[Time3],IIf(NZ([
Time4])>NZ([Time5]),[Time4],IIf(NZ([Time5])>NZ([Time6]),[Time5],IIf(NZ([Time6])
>NZ([Time7]),[Time6],IIf(NZ([Time7])>NZ([Time8]),[Time7],[Time8])))))) AS Tmax,
TI.CarbSh2, TI.CarbSh3, TI.CarbSh4, TI.CarbSh5, TI.CarbSh6, TI.CarbSh7,
TI.CarbSh8,
NZ([CarbSh2])+NZ([CarbSh3])+NZ([CarbSh4])+NZ([CarbSh5])+NZ([CarbSh6])+NZ([
CarbSh7])+NZ([CarbSh8]) AS CarbShTot,
IIf([Time2]=[Tmax],[CarbSh2],0)+IIf([Time3]=[Tmax],[CarbSh3],0)+IIf([Time4]=[Tma
x],[Carbsh4],0)+IIf([Time5]=[Tmax],[CarbSh5],0)+IIf([Time6]=[Tmax],[CarbSh6],0)+II
f([Time7]=[Tmax],[CarbSh7],0)+NZ([CarbSh8]) AS CarbShLast,
TI.MealIns2, TI.MealIns3, TI.MealIns4, TI.MealIns5, TI.MealIns6, TI.MealIns7,
TI.MealIns8,
TI.AMCorIns2, TI.AMCorIns3, TI.AMCorIns4, TI.AMCorIns5, TI.AMCorIns6,
TI.AMCorIns7,
TI.AMCorIns8,
TI.TBCorIns2, TI.TBCorIns3, TI.TBCorIns4, TI.TBCorIns5, TI.TBCorIns6,
TI.TBCorIns7, TI.TBCorIns8,
NZ([TBCorIns2])+NZ([TBCorIns3])+NZ([TBCorIns4])+NZ([TBCorIns5])+NZ([TBCor
Ins6])+NZ([TBCorIns7])+NZ([TBCorIns8]) AS TBCorTot,
[MealIns2]+[AMCorIns2] AS eMealIns2
[MealIns3]+[AMCorIns3] AS eMealIns3
[MealIns4]+[AMCorIns4] AS eMealIns4
[MealIns5]+[AMCorIns5] AS eMealIns5
[MealIns6]+[AMCorIns6] AS eMealIns6
[MealIns7]+[AMCorIns7] AS eMealIns7
[MealIns8]+[AMCorIns8] AS eMealIns8
```

-continued

NZ([eMealIns2])+NZ([eMealIns3])+NZ([eMealIns4])+NZ([eMealIns5])+NZ([eMealIns6])+NZ([eMealIns7])+NZ([eMealIns8]) AS eMealInsTot,
IIf([Time2]=[Tmax],NZ([eMealIns2]),0)+IIf([Time3]=[Tmax],NZ([eMealIns3]),0)+IIf([Time4]=[Tmax],NZ([eMealIns4]),0)+IIf([Time5]=[Tmax],NZ([eMealIns5]),0)+IIf([Time6]=[Tmax],NZ([eMealIns6]),0)+IIf([Time7]=[Tmax],NZ([eMealIns7]),0)+NZ([eMealIns8]) AS eMealInsLast,
[Time2]+24−[tmax] AS dt0,
IIf(NZ([Time2])>0,[time2]−[time1],0) AS dt1,
IIf(NZ([Time3])>0,[time3]−[time2],0) AS dt2,
IIf(NZ([Time4])>0,[time4]−[time3],0) AS dt3,
IIf(NZ([Time5])>0,[time5]−[time4],0) AS dt4,
IIf(NZ([Time6])>0,[time6]−[time5],0) AS dt5,
IIf(NZ([Time7])>0,[time7]−[time6],0) AS dt6,
IIf(NZ([Time8])>0,[time8]−[time7],0) AS dt7,
TI.BR1, TI.BR2, TI.BR3, TI.BR4, TI.BR5, TI.BR6, TI.BR7, TI.BR8,
[BR1]*[dt0] AS Basl0,
[BR2]*[dt2] AS Basl2,
[BR3]*[dt3] AS Basl3,
[BR4]*[dt4] AS Basl4,
[BR5]*[dt5] AS Basl5,
[BR6]*[dt6] AS Basl6,
[BR7]*[dt7] AS Basl7,
NZ([Basl7])+NZ([Basl6])+NZ([Basl5])+NZ([Basl4])+NZ([Basl3])+NZ([Basl2])+NZ([Basl0]) AS Basal,
TI.BG2, TI.BG3, TI.BG4, TI.BG5, TI.BG6, TI.BG7, TI.BG8,
TI.CIR1, TI.CIR2, TI.CIR3, TI.CIR4, TI.CIR5, TI.CIR6, TI.CIR7, TI.CIR8,
IIf([Time2]=[Tmax],[CIR2],0)+IIf([Time3]=[Tmax],[CIR3],0)+IIf([Time4]=[Tmax],[CIR4],0)+IIf([Time5]=[Tmax],[CIR5],0)+IIf([Time6]=[Tmax],[CIR6],0)+IIf([Time7]=[Tmax],[CIR7],0)+NZ([CIR8]) AS CIRLast,
TI.deRxIns1,
TI.deMealIns,
[deRxIns1]−[deMealIns] AS dBasal,
[CarbShTot]/([eMealInsTot]−[BasalRxTot] + [BasTot] − [dRxIns1] AS CIRecC,
TI.CIRrx,
IIf(0<=[deRxIns1]/[CorTot]<=1,0,1) AS swtch,
([Basl0]+[swtch]*[TBCorIns2]+([deRxIns1]−[swtch]*[TBCorTot])*([TBCorIns2]+[swtch]*[Basl0])
/([TBCorTot]+[swtch]*[BaslTot])−[deMealIns]*[eMealInsLast]/[eMealInsTot])/[dt0] AS BRrecA0,
[BRrecA0] AS BRrecA1,
([Basl2]+[swtch]*[TBCorIns3]+([deRxIns1]−[swtch]*[TBCorTot])*([TBCorIns3]+[swtch]*[Basl2])
/([TBCorTot]+[swtch]*[BaslTot])−[deMealIns]*NZ([eMealIns2])/[eMealInsTot])/[dt2]
AS BRrecA2,
([Basl3]+[swtch]*[TBCorIns4]+([deRxIns1]−[swtch]*[TBCorTot])*([TBCorIns4]+[swtch]*[Basl3])
/([TBCorTot]+[swtch]*[BaslTot])−[deMealIns]*NZ([eMealIns3])/[eMealInsTot])/[dt3]
AS BRrecA3,
([Basl4]+[swtch]*[TBCorIns5]+([deRxIns1]−[swtch]*[TBCorTot])*([TBCorIns5]+[swtch]*[Basl4])
/([TBCorTot]+[swtch]*[BaslTot])−[deMealIns]*NZ([eMealIns4])/[eMealInsTot])/[dt4]
AS BRrecA4,
([Basl5]+[swtch]*[TBCorIns6]+([deRxIns1]−[swtch]*[TBCorTot])*([TBCorIns6]+[swtch]*[Basl5])
/([TBCorTot]+[swtch]*[BaslTot])−[deMealIns]*NZ([eMealIns5])/[eMealInsTot])/[dt5]
AS BRrecA5,
([Basl6]+[swtch]*[TBCorIns7]+([deRxIns1]−[swtch]*[TBCorTot])*([TBCorIns7]+[swtch]*[Basl6])
([TBCorTot]+[swtch]*[BaslTot])−[deMealIns]*NZ([eMealIns6])/[eMealInsTot])/[dt6]
AS BRrecA6,
([Basl7]+[swtch]*[TBCorIns8]+([deRxIns1]−[swtch]*[TBCorTot])*([TBCorIns8]+[swtch]*[Basl7])
/([TBCorTot]+[swtch]*[BaslTot])−[deMealIns]*NZ([eMealIns7])/[eMealInsTot])/[dt7]
AS BRrecA7,
TI.BRrx1, TI.BRrx2, TI.BRrx3, TI.BRrx4, TI.BRrx5, TI.BRrx6, TI.BRrx7, TI.BRrx8,
0 AS TimeRx1,
TI.TimeRx2, TI.TimeRx3, TI.TimeRx4, TI.TimeRx5, TI.TimeRx6, TI.TimeRx7, TI.TimeRx8,
IIf(NZ([TimeRx2])>NZ([TimeRx3]),[TimeRx2],IIf(NZ([TimeRx3])>NZ([TimeRx4]),[TimeRx3],IIf(NZ([TimeRx4])>NZ([TimeRx5]),[TimeRx4],IIf(NZ([TimeRx5])>NZ([TimeRx6]),[TimeRx5],IIf(NZ([TimeRx6])>NZ([TimeRx7]),[TimeRx6],IIf(NZ([TimeRx7])>NZ([TimeRx8]),[TimeRx7],[TimeRx8]))))))) AS TRxmax,
IIf(NZ([TimeRx2])>0,[TimeRx2]+24−[Trxmax],0) AS dTrx0,
IIf(NZ([TimeRx2])>0,[TimeRx2]−[TimeRx1],0) AS dTrx1,
IIf(NZ([TimeRx3])>0,[TimeRx3]−[TimeRx2],0) AS dTrx2,
IIf(NZ([TimeRx4])>0,[TimeRx4]−[TimeRx3],0) AS dTrx3,
IIf(NZ([TimeRx5])>0,[TimeRx5]−[TimeRx4],0) AS dTrx4,
IIf(NZ([TimeRx6])>0,[TimeRx6]−[TimeRx5],0) AS dTrx5,
IIf(NZ([TimeRx7])>0,[TimeRx7]−[TimeRx6],0) AS dTrx6, -continued

```
IIf(NZ([TimeRx8])>0,[TimeRx8]-[TimeRx7],0) AS dTrx7,
[CarbShLast]/([eMealInsLast]+[deRxIns1]*[TBCorIns2]/[TBCorTot]-([BRrx1]-
[BR1])*[dt0]) AS CIRrec0,
[CarbSh2]/([eMealIns2]+[deRxIns1]*[TBCorIns3]/[TBCorTot]-([BRrx2]-[BR2])*[dt2])
AS CIRrec2, [CarbSh3]/([eMealIns3]+[deRxIns1]*[TBCorIns4]/[TBCorTot]-([BRrx3]-
[BR3])*[dt3]) AS CIRrec3,
[CarbSh4]/([eMealIns4]+[deRxIns1]*[TBCorIns5]/[TBCorTot]-([BRrx4]-[BR4])*[dt4])
AS CIRrec4, [CarbSh5]/([eMealIns5]+[deRxIns1]*[TBCorIns6]/[TBCorTot]-([BRrx5]-
[BR5])*[dt5]) AS CIRrec5,
[CarbSh6]/([eMealIns6]+[deRxIns1]*[TBCorIns7]/[TBCorTot]-([BRrx6]-[BR6])*[dt6])
AS CIRrec6, [CarbSh7]/([eMealIns7]+[deRxIns1]*[TBCorIns8]/[TBCorTot]-([BRrx7]-
[BR7])*[dt7]) AS CIRrec7,
TI.eMealInsRx1, TI.eMealInsRx2, TI.eMealInsRx3, TI.eMealInsRx4, TI.eMealInsRx5,
TI.eMealInsRx6, TI.eMealInsRx7,
TI.CIRrx1, TI.CIRrx2, TI.CIRrx3, TI.CIRrx4, TI.CIRrx5, TI.CIRrx6, TI.CIRrx7,
TI.CIRrx8, TI.InptFormType
FROM TP INNER JOIN TI ON TP.PatientID = TI.Tp_PatientID
ORDER BY TI.IntrDate DESC;
```

We claim:

1. A computer-implemented method of dynamically adjusting an insulin dosing scheme of a subject in an insulin pump, comprising:
   obtaining, by at least one computing device implemented in the insulin pump and comprising at least one hardware processor, data comprising a previous insulin dosing scheme of the subject and blood glucose data of the subject relating to the previous insulin dosing scheme; and
   determining, by the at least one computing device, an adjusted insulin dosing scheme for the subject based on the data and the previous insulin dosing scheme, the adjusted insulin dosing scheme comprising:
   (a) combining, by the at least one computing device, a base insulin dosage administered over a given previous time interval (Basal Insulin) with an additional insulin dosage administered in relation to a meal taken during the previous given time interval (Meal Insulin) to determine a previous total insulin prescribed for the given time interval (Prescription Insulin);
   (b) determining, by the at least one computing device, an error in the previous total insulin prescribed by determining a difference between previous blood glucose data and a blood glucose target, dividing the difference by a Correction Factor (CF), applying a fraction of the divided difference to determine the error, and applying a portion of said error to Meal Insulin and a portion of the error to Basal Insulin, by either:
   (i): determining, by the at least one computing device, a preliminary desired change to Meal Insulin as an independent variable and then determining a change to Basal Insulin as a dependent variable, wherein the change to Basal Insulin is calculated as the error in the previous total insulin prescribed less the preliminary desired change to Meal Insulin, or
   (ii): determining, by the at least one computing device, a preliminary desired change Basil Insulin as an independent variable and then determining a change to Meal Insulin as a dependent variable, wherein the change to Meal Insulin is calculated as the error in the previous total insulin prescribed less the preliminary desired change to Meal Insulin; and
   (c) determining, by the at least one computing device, a change to a Carbohydrate-to-Insulin Ratio (CIR) to be used in adjusting the insulin dosing scheme to arrive at an adjusted insulin dosing scheme either by:
   (i) multiplying, by the at least one computing device, the change to Meal Insulin by a rate of change of the Carbohydrate-to-Insulin Ratio (CIR) with respect to Meal Insulin, which is determined as a calculus derivative of a population-based correlation, or
   (ii) determining, by the at least one computing device, a change for the Carbohydrate-to-Insulin Ratio (CIR) for a 24 hour period based on a combination of a total Meal Insulin for the 24 hour period plus the error in the previous total insulin prescribed for the 24 hour period minus a change for Basal Insulin for the 24 hour period, and dividing a total amount of carbohydrates for the 24 hour period by the combination; and
   causing, by the at least one computing device, the adjusted insulin dosing scheme determined for the subject to be shown in a display of an insulin device comprising the insulin pump for an implementation of the adjusted insulin dosing scheme; and
   administering, by the insulin device, at least a portion of the insulin to the subject in accordance with the adjusted insulin dosing scheme.

2. The computer-implemented method of claim 1, wherein the adjusted insulin scheme is comprised of one or more adjusted values for a daily schedule of Basal Rates, a daily schedule of Carbohydrate-to-Insulin Ratios, a daily schedule of Meal Insulin doses, or one or more values of Correction Factor (CF).

3. The computer-implemented method of claim 1, further comprising rendering, by the at least one computing device, the adjusted insulin dosing scheme in a video screen, generating, by the at least one computing device, a printed report, generating, by the at least one computing device, a digital file, or communicating, by the at least one computing device, the adjusted insulin dosing scheme to an operating program of the insulin pump.

4. An insulin pump configured to dynamically adjust an insulin dosing scheme of a subject, comprising:
   an insulin cartridge comprising insulin;
   an infusion set configured to provide the insulin from the insulin cartridge into the subject through a cannula;
   a battery;

at least one computing device comprising at least one hardware processor; and program instructions executable in the at least one computing device that, when executed, cause the at least one computing device to determine a rate at which insulin is introduced into the subject by:

accessing data comprising a previous insulin dosing scheme of the subject and blood glucose data of the subject relating to the previous insulin dosing scheme; and determining an adjusted insulin dosing scheme for the subject based on the data, the adjusted insulin dosing scheme comprising:

(a) combining a base insulin dosage administered over a previous given time interval (Basal Insulin) with an additional insulin dosage administered in relation to a meal taken during the previous given time interval (Meal Insulin) to determine a previous total insulin prescribed for the given time interval (Prescription Insulin), (b) determining an error in the previous total insulin prescribed by determining a difference between previous blood glucose data and a blood glucose target, dividing the difference by a Correction Factor (CF), applying a fraction of the divided difference to determine the error, and applying a portion of the error to Meal Insulin and a portion of the error to Basal Insulin, by either of two methods of:

(i) determining a preliminary desired change to Meal Insulin as an independent variable and then determining a change to Basal Insulin as a dependent variable, wherein the change to Basal Insulin is calculated as the error in the previous total insulin prescribed less the preliminary desired change to Meal Insulin, or (ii): determining a preliminary desired change to Basil Insulin as an independent variable and then determining a change to Meal Insulin as a dependent variable, wherein the change to Meal Insulin is calculated as the error in the previous total insulin prescribed less the preliminary desired change to Meal Insulin; and (c) determining a change to a Carbohydrate-to-Insulin Ratio (CIR) to be used in adjusting the insulin dosing scheme to arrive at an adjusted insulin dosing scheme either by:

(i) multiplying the change to Meal Insulin by a rate of change of the Carbohydrate-to-Insulin Ratio (CIR) with respect to Meal Insulin, which is determined as a calculus derivative of a population-based correlation, or (ii) determining a change for the Carbohydrate-to-Insulin Ratio (CIR) for a 24 hour period based on a combination of a total Meal Insulin for the 24 hour period plus the error in the previous total insulin prescribed for the 24 hour period minus a change for Basal Insulin for the 24 hour period, and dividing a total amount of carbohydrates for the 24 hour period by the combination; and providing, via the infusion set, at least a portion of the insulin to the subject in accordance with the adjusted insulin dosing scheme determined for the subject.

5. The insulin pump of claim 4, wherein the adjusted insulin scheme is comprised of one or more adjusted values for a daily schedule of Basal Rates, a daily schedule of Carbohydrate-to-Insulin Ratios, a daily schedule of Meal Insulin doses, or one or more values of Correction Factor (CF).

6. The insulin pump of claim 4, further comprising program instructions that, when executed, cause the at least one computing device to render the adjusted insulin dosing scheme in a video screen of an electronic display, generate a printed report, generate a digital file, or communicate the adjusted insulin dosing scheme to an operating program of the insulin pump.

7. The computer-implemented method of claim 1, wherein the change to Carbohydrate-to-Insulin Ratio of step(c)(i) is determined as the rate of change of CIR with respect to a total insulin dose for a 24 hour period times the rate of change of the total insulin dose for the 24 hour period with respect to Meal Insulin for the 24 hour period.

8. The insulin pump of claim 4, wherein the change to Carbohydrate-to-Insulin Ratio of step(c)(i) is determined as the rate of change of CIR with respect to a total insulin dose for a 24 hour period times the rate of change of the total insulin dose for the 24 hour period with respect to Meal Insulin for the 24 hour period.

9. A system, comprising:

at least one computing device comprising at least one hardware processor;

an insulin device comprising a display and an insulin pump; and an application executable in the at least one computing device that, when executed, causes the at least one computing device to:

access data comprising a previous insulin dosing scheme of a subject and blood glucose data of the subject relating to the previous dosing scheme; and determine an adjusted insulin dosing scheme for the subject based on an analysis of the data performed by the at least one computing device, the adjusted insulin dosing scheme comprising:

(a) combining a base insulin dosage administered over a previous given time interval (Basal Insulin) with an additional insulin dosage administered in relation to a meal taken during the previous given time interval (Meal Insulin) to determine a previous total insulin prescribed for the given time interval (Prescription Insulin), (b) determining an error in the previous total insulin prescribed by determining a difference between previous blood glucose data and a blood glucose target, dividing the difference by a Correction Factor (CF), applying a fraction of the divided difference to determine the error, and applying a portion of the error to Meal Insulin and a portion of the error to Basal Insulin, by either:

(i) determining a preliminary desired change to Meal Insulin as an independent variable and then determining a change to Basal Insulin as a dependent variable, wherein the change to Basal Insulin is calculated as the error in the previous total insulin prescribed less the preliminary desired change to Meal Insulin, or (ii): determining a preliminary desired change to Basil Insulin as an independent variable and then determining a change to Meal Insulin as a dependent variable, wherein the change to Meal Insulin is calculated as the error in the previous total insulin prescribed less the preliminary desired change to Meal Insulin; and (c) determining a change to a Carbohydrate-to-Insulin Ratio (CIR) to be used in determining the adjusted insulin dosing scheme either by:
  (i) multiplying the change to Meal Insulin by a rate of change of the Carbohydrate-to-Insulin Ratio (CIR) with respect to Meal Insulin, which is determined as a calculus derivative of a population-based correlation, or
  (ii) determining a change for the Carbohydrate-to-Insulin Ratio (CIR) for a 24 hour period based on a combination of a total Meal Insulin for the 24 hour period plus the error in the previous total insulin prescribed for the 24 hour period minus a change for Basal Insulin for the 24 hour period, and dividing a total amount of carbohydrates for the 24 hour period by the combination; and causing, by the at least one computing device, the adjusted insulin dosing scheme determined for the subject to be shown in the display of the insulin device for an implementation of the adjusted insulin dosing scheme; and administering, by the insulin device, at least a portion of the insulin to the subject in accordance with the adjusted insulin dosing scheme determined for the subject.

10. The system of claim 9, wherein the adjusted insulin scheme is comprised of one or more adjusted values for a daily schedule of Basal Rates, a daily schedule of Carbohydrate-to-Insulin Ratios, a daily schedule of Meal Insulin doses, or one or more values of Correction Factor (CF).

11. The system of claim 9, wherein causing the insulin pump to provide at least the portion of the insulin to the subject in accordance with the adjusted insulin dosing scheme further comprises causing the insulin device to pump the insulin from an insulin cartridge into the subject through a cannula.

12. The system of claim 9, wherein the application, when executed, further causes the at least one computing device to render the adjusted insulin dosing scheme in a video screen, generate a printed report, generate a digital file, or communicate the adjusted insulin dosing scheme to an operating program of the insulin pump.

13. The system of claim 9, wherein the change to Carbohydrate-to-Insulin Ratio of step(c)(i) is determined as the rate of change of CIR with respect to a total insulin dose for a 24 hour period times the rate of change of the total insulin dose for the 24 hour period with respect to Meal Insulin for the 24 hour period.

14. The computer-implemented method of claim 1, wherein the previous insulin dosing scheme is comprised of one or more values for a daily schedule of Basal Rates, a daily schedule of Carbohydrate-to-Insulin Ratios, a daily schedule of Meal Insulin doses, or one or more values of Correction Factor (CF).

15. The insulin pump of claim 4, wherein the previous insulin dosing scheme is comprised of one or more values for a daily schedule of Basal Rates, a daily schedule of Carbohydrate-to-Insulin Ratios, a daily schedule of Meal Insulin doses, or one or more values of Correction Factor (CF).

16. The system of claim 9, wherein the previous insulin dosing scheme is comprised of one or more values for a daily schedule of Basal Rates, a daily schedule of Carbohydrate-to-Insulin Ratios, a daily schedule of Meal Insulin doses, or one or more values of Correction Factor (CF).

* * * * *